(12) United States Patent
Gabriele et al.

(10) Patent No.: US 11,896,575 B2
(45) Date of Patent: Feb. 13, 2024

(54) TRANSDERMAL FORMULATION FOR DELIVERY OF HYDROPHOBIC COMPOUNDS AND PROCESS FOR THE PREPARATION THEREOF

(71) Applicant: Delivra Inc., Burlington (CA)

(72) Inventors: Joseph Gabriele, Stoney Creek (CA); Mikaela Teris, Montreal (CA)

(73) Assignee: Delivra Inc., Burlington (CA)

(*) Notice: Subject to any disclaimer, the term of this patent is extended or adjusted under 35 U.S.C. 154(b) by 588 days.

(21) Appl. No.: 16/756,689

(22) PCT Filed: Oct. 16, 2018

(86) PCT No.: PCT/CA2018/051302
§ 371 (c)(1),
(2) Date: Apr. 16, 2020

(87) PCT Pub. No.: WO2019/075558
PCT Pub. Date: Apr. 25, 2019

(65) Prior Publication Data
US 2020/0237714 A1    Jul. 30, 2020

Related U.S. Application Data

(60) Provisional application No. 62/572,744, filed on Oct. 16, 2017.

(51) Int. Cl.
| | |
|---|---|
| *A61K 31/352* | (2006.01) |
| *A61K 9/00* | (2006.01) |
| *A61K 9/107* | (2006.01) |
| *A61K 31/05* | (2006.01) |
| *A61K 31/137* | (2006.01) |
| *A61K 31/167* | (2006.01) |
| *A61K 31/445* | (2006.01) |
| *A61K 31/485* | (2006.01) |
| *A61K 47/14* | (2017.01) |
| *A61K 47/22* | (2006.01) |
| *A61K 47/24* | (2006.01) |
| *A61K 47/36* | (2006.01) |
| *A61K 47/38* | (2006.01) |

(52) U.S. Cl.
CPC ............ *A61K 31/352* (2013.01); *A61K 9/006* (2013.01); *A61K 9/0014* (2013.01); *A61K 9/0031* (2013.01); *A61K 9/107* (2013.01); *A61K 31/05* (2013.01); *A61K 31/137* (2013.01); *A61K 31/167* (2013.01); *A61K 31/445* (2013.01); *A61K 31/485* (2013.01); *A61K 47/14* (2013.01); *A61K 47/22* (2013.01); *A61K 47/24* (2013.01); *A61K 47/36* (2013.01); *A61K 47/38* (2013.01)

(58) Field of Classification Search
CPC .... A61K 31/352; A61K 31/05; A61K 31/137; A61K 31/167; A61K 31/445; A61K 31/485; A61K 47/14; A61K 47/22; A61K 47/24; A61K 47/36; A61K 47/38
See application file for complete search history.

(56) References Cited

U.S. PATENT DOCUMENTS

| | | | |
|---|---|---|---|
| 5,043,323 A | 8/1991 | Bombardelli et al. | |
| 2011/0021439 A1 | 1/2011 | Amari et al. | |

FOREIGN PATENT DOCUMENTS

| | | |
|---|---|---|
| CA | 2994331 | 2/2017 |
| CA | 2995605 | 2/2017 |
| CA | 2997220 | 3/2017 |
| CA | 2997842 | 3/2017 |
| CA | 2952335 | 6/2017 |
| CA | 3024205 | 11/2017 |
| WO | 2017020125 | 2/2017 |

OTHER PUBLICATIONS

Chen et al., "Natural Terpenes as Penetration Enhancers for Transdermal Drug Delivery". Molecules, vol. 21(1709), pp. 1-21 (2016).
Dragicevic et al., "Chapter 2: Chemical Penetration Enhancers: Classification and Mode of Action Chemical Methods in Penetration Enhancement". Percutaneous Penetration Enhancers—Chemical Methods in Penetration Enhancement, pp. 11-28, ISBN 978-3-662-47039-8 (eBook) Section 2.5.1 "Terpenes" (2015).
Lim et al., "A Review on Terpenes as Skin Penetration Enhancers in Transdermal Drug Delivery". Journal of Essential Oil Research, vol. 21(5), pp. 423-428 (2011).
Prausnitz et al., "Transdermal Drug Delivery". Nat. Biotechnol., 26(11):1261-1268 (2008).
International Search Report and Written Opinion dated Dec. 19, 2018 in International Application No. PCT/CA2018/051302.
European Search Report dated Jun. 11, 2021 in European Application No. 18868840.2.

*Primary Examiner* — Sahar Javanmard
(74) *Attorney, Agent, or Firm* — Procopio, Cory, Hargreaves & Savitch LLP

(57) ABSTRACT

The present application includes a transdermal base formulation useful for example, for the transdermal delivery of active pharmaceutical ingredients along with a process for preparation thereof. In particular, the transdermal base formulation comprises: (a) an aqueous phase comprising water and at least one emulsion stabilizer; (b) an oil phase comprising at least one emulsifier, at least one emulsion stabilizer, at least one emollient comprising at least one flavonoid, at least one other emollient, and a terpene-rich natural butter; (c) an external phase comprising at least one terpene-rich extract or oil, at least one penetration enhancer and a phospholipid-complexed flavonoid; and optionally (d) at least one preservative phase.

20 Claims, 5 Drawing Sheets

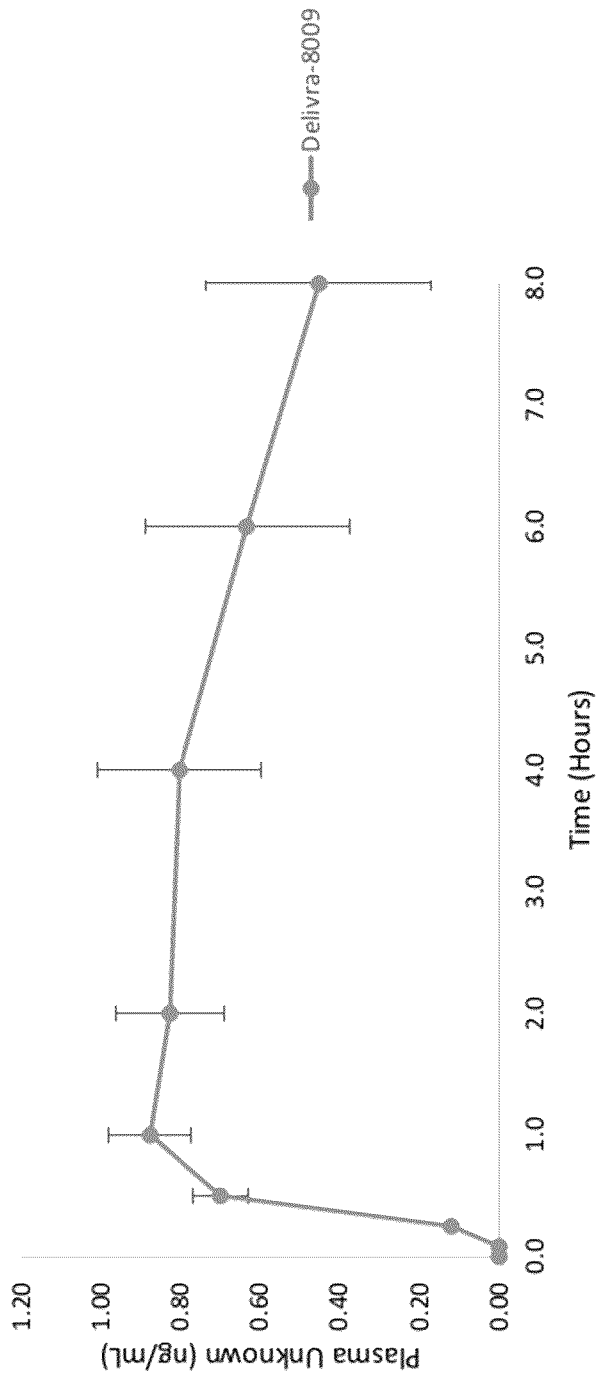

TRANSDERMAL FORMULATION FOR DELIVERY OF HYDROPHOBIC COMPOUNDS AND PROCESS FOR THE PREPARATION THEREOF

CROSS-REFERENCE TO RELATED APPLICATIONS

The present application claims the benefit of priority from co-pending U.S. Provisional Patent Application No. 62/572,744, Filed Oct. 16, 2017, the contents of which are incorporated herein by reference in its entirety.

FIELD

The present application relates to emulsion-based transdermal formulations for the delivery of active agents. In particular, the present application relates to emulsion-based formulations comprising terpenes for the transdermal delivery of hydrophobic active agents.

BACKGROUND

The premature metabolism of drugs as a result of the first-pass effect has made transdermal delivery an attractive and alternative strategy (Prausnitz, M. R., Langer, R. "Transdermal Drug Delivery. Nat. Biotechnol. 2008, 26(11): 1261-1268). For many years, people have placed natural substances on the skin for local ailments. However, lending this strategy towards all therapeutic drugs is not feasible. The human skin acts as a formidable barrier due in large part to the stratum corneum, which mostly consists of a lipid-enriched matrix and blocks entry of most topically applied agents, with the exception of low molecular weight, lipid-soluble drugs. This poses a challenge for administrating medications via the skin for either local cutaneous or systemic therapy.

Transdermal drug delivery strategies have thus focused primarily on the manipulation of this lipid milieu. In particular, penetration enhancers which interact with skin constituents to promote drug transport have provided an approach to increase the range of therapeutic agents that can be delivered.

Despite the significant permeability barrier of the stratum corneum, drug delivery via the skin is a very attractive option and is widely employed for both local and systemic therapy. Topical treatment of cutaneous disorders obviously targets the site of disease, thereby minimizing adverse side effects elsewhere within the body. Delivery of systemic therapies via the skin avoids degradation of the medication within the gastrointestinal tract and first-pass metabolism by the liver, both of which are associated with oral administration of drugs, in addition to evading the pain and safety issues associated with injections. Transdermal delivery of drugs, in some cases, enables infrequent dosing and maintenance of steady state drug levels.

Many pharmaceutically active compounds intended for oral or transdermal administration are poorly soluble in water providing a challenge to formulate these drugs in a drug delivery system that exhibits the desirable pharmacokinetic profiles in vivo. Poor oral bioavailability may lead to ineffective therapy, the need for higher dosing and/or undesirable side effects. As well, pharmaceutical preparations with relatively short half-lives require frequent dosing at the expense of patient inconvenience and higher therapy costs.

For example, the plant family Cannabaceae has been investigated for its medicinal and psychoactive properties for several hundred years, however the recreational, medical, and structure-activity relationships of the compounds responsible for these effects have come to light within the mid-$20^{th}$ century and beyond. *Cannabis sativa* is the most commonly investigated plant species and despite the existence of ~113 cannabinoid compounds, the vast majority of research is focused upon the psychoactive Tetrahydrocannabinol (THC) and the structurally similar non-psychoactive Cannabidiol (CBD).

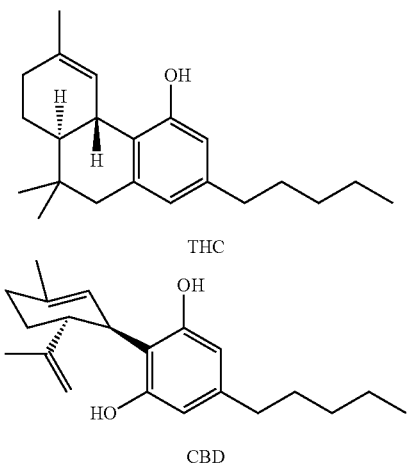

SUMMARY

In the present application, a base formulation that is used, for example, for the transdermal delivery of hydrophobic active agents (such as pharmaceutical agents), is disclosed along with a process for its preparation. In one embodiment, the formulation is an emulsion-based formulation which comprises terpene compounds for the transdermal delivery of hydrophobic compounds. In some embodiments, the formulation comprises at least one oil phase comprising terpenes, at least one aqueous phase, and at least one external phase comprising terpenes.

In some embodiments, the present application includes a transdermal formulation comprising:

(a) an aqueous phase comprising water and at least one emulsion stabilizer;

(b) an oil phase comprising at least one emulsifier, at least one emulsion stabilizer, at least one emollient comprising at least one flavonoid, at least one other emollient, and a terpene-rich natural butter;

wherein the oil and aqueous phase form an emulsion;

(c) at least one external phase comprising at least one terpene-rich extract or oil, at least one penetration enhancer and a phospholipid-complexed flavonoid; and optionally (d) at least one preservative phase.

In some embodiments, the present application includes a process for preparing a transdermal delivery formulation as described herein comprising:

(a) heating an aqueous phase comprising water and at least one emulsion stabilizer to a first temperature;

(b) heating an oil phase comprising at least one emulsifier, at least one emulsion stabilizer, at least one emollient comprising at least one flavonoid, at least one other emollient, and a terpene-rich natural butter to the first temperature;

(c) adding the aqueous phase to the oil phase with stirring at the first temperature and continuing to stir at the first temperature until an emulsion is formed;

(d) cooling the emulsion in (c) to a second temperature; and, in any order:

(e) adding one or more external phases comprising at least one penetration enhancer, at least one terpene-rich extract or oil, and a phospholipid-complexed flavonoid to the emulsion at the second temperature; and optionally (f) adding one or more preservative phases to the emulsion.

The present disclosure also includes formulations comprising a polar oil, an oily vehicle and an active ingredient comprising a hydrophobic compound.

In one embodiment of the disclosure, there is provided a formulation comprising:
  i) at least one polar oil;
  ii) an oily vehicle comprising mono-, di- and triglycerides;
  iii) a penetration enhancer; and
  iv) an active ingredient comprising a hydrophobic compound.

In one embodiment of the disclosure, the formulation comprises:
  i) at least one polar oil;
  ii) an oily vehicle comprising mono-, di- and triglycerides;
  iii) a penetration enhancer; and
  iv) an active ingredient comprising a cannabinoid.

The present disclosure includes methods for treating diseases and conditions comprising administering an effective amount of one or more of the formulations of the application to a subject in need thereof.

The present disclosure also includes methods for treating one or more cannabinoid-responsive diseases and conditions comprising administering an effective amount of one or more of the formulations of the application to a subject in need thereof.

The present disclosure also includes a use of the formulations described herein for the delivery of cannabinoids for the treatment of one or more one or more cannabinoid-responsive diseases and conditions.

In some embodiments, the cannabinoid-responsive disease or condition is pain, for example, chronic pain or neuropathic pain. In one embodiment, the cannabinoid-responsive disease or condition is a neurological disorder, such as epilepsy, or epilepsy related symptoms.

In one embodiment, the formulations of the disclosure are for transdermal formulation, buccal administration for the mouth (mucosa) or rectal administration (mucosa).

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

BRIEF DESCRPITION OF THE FIGURES

The description will now be described with references to the figures in which

FIG. 5 shows the pharmacokinetics of a cannabinoid using a topical cannabis formulation in a further embodiment of the disclosure.

DETAILED DESCRIPTION

I. Definitions

Figure 1:
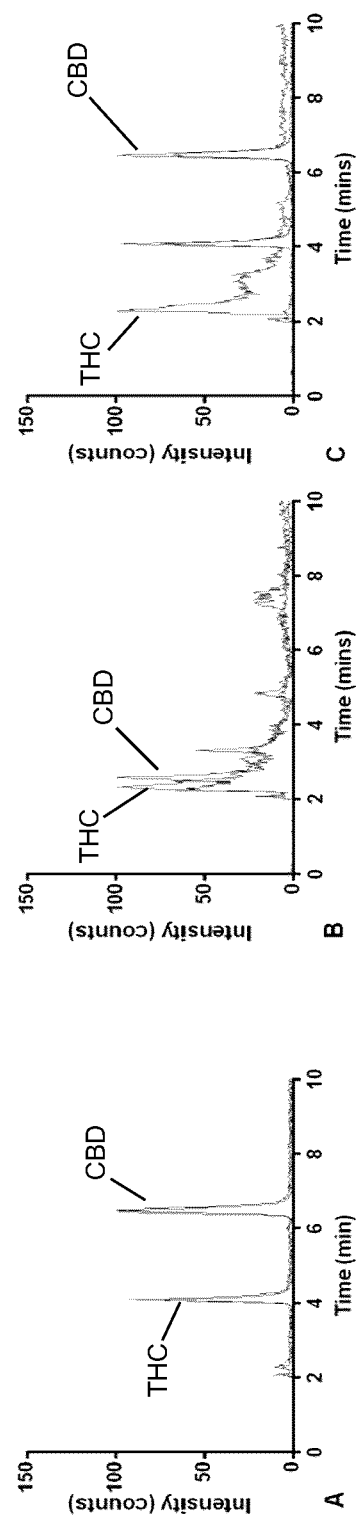
FIG. 1 shows LC-MS/MS profiles of certain analytes.

Unless otherwise indicated, the definitions and embodiments described in this and other sections are intended to be applicable to all embodiments and aspects of the present application herein described for which they are suitable as would be understood by a person skilled in the art.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this application and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The present description refers to a number of chemical terms and abbreviations used by those skilled in the art. Nevertheless, definitions of selected terms are provided for clarity and consistency.

As used in this application, the singular forms "a", "an" and "the" include plural references unless the content clearly dictates otherwise. For example, an embodiment including "an agent" should be understood to present certain aspects with one agent or two or more additional agents.

In embodiments comprising an "additional" or "second" component, such as an additional or second agent, the second component as used herein is chemically different from the other components or first component. A "third" component is different from the other, first, and second components, and further enumerated or "additional" components are similarly different.

The term "agent" as used herein indicates a compound or mixture of compounds that, when added to a formulation, tend to produce a particular effect on the formulation's properties.

The term "active agent" or "active pharmaceutical ingredient" or "API" as used herein means an agent or a mixture of agents that causes the desired therapeutic effect. The active agent may be a pharmaceutical agent and/or a natural product ingredient which causes a desired therapeutic effect.

The term "hydrophobic," as used herein refers to compounds, agents or active agents which lack an affinity for water.

The term "buffering agent" as used herein refers to a compound or mixture of compounds that adjusts the pH of the formulation.

The term "and/or" as used herein means that the listed items are present, or used, individually or in combination. In effect, this term means that "at least one of" or "one or more" of the listed items is used or present.

The term "suitable" as used herein means that the selection of the particular compound or conditions would depend on the specific process step to be performed, and the identity of the compounds involved, but the selection would be well within the skill of a person trained in the art. All process/method steps described herein are to be conducted under conditions sufficient to provide the desired transformation. A person skilled in the art would understand that all process conditions, including, for example, solvent, time, temperature, pressure, component ratio and whether or not the step should be performed under an anhydrous or inert atmosphere, can be varied to optimize the yield of the desired product and it is within their skill to do so.

"Formulation" and "pharmaceutical formulation" as used herein are equivalent terms referring to a formulation for pharmaceutical use.

The term "pharmaceutically acceptable" means compatible with the treatment of animals, in particular, humans.

The term "effective amount" as used herein means an amount sufficient to achieve the desired result and accordingly will depend on the ingredient and its desired result. Nonetheless, once the desired effect is known, determining the effective amount is within the skill of a person skilled in the art.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilizing (i.e. not worsening) the state of disease, prevention of disease spread, delaying or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment. "Treating" and "treatment" as used herein also include prophylactic treatment. Treatment methods comprise administering to a subject a therapeutically effective amount of an active agent and optionally consists of a single administration, or alternatively comprises a series of applications. The length of the treatment period depends on a variety of factors, such as the severity of the condition, the age of the patient, the concentration of active ingredient or agent, the activity of the compositions described herein, and/or a combination thereof. It will also be appreciated that the effective dosage of the agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient.

"Topical composition" as used herein includes a composition that is suitable for topical application to the skin, nail, mucosa, wound bed or wound cavity. A topical composition may, for example, be used to confer a therapeutic or cosmetic benefit to its user. Specific topical compositions can be used for local, regional, or transdermal application of substances.

The term "topical administration" is used herein to include the delivery of a substance, such as a therapeutically active agent, to the skin or a localized region of the body.

The term "buccal administration" as used herein refers to application to the oral cavity involves surfaces of, near, relating to, or lying in the mouth, under the tongue (sublingual) or cheek.

"Transdermal" as used herein includes a process that occurs through the skin. The terms "transdermal," "percutaneous" and "transcutaneous" can be used interchangeably. In certain embodiments, "transdermal" also includes epicutaneous. Transdermal administration is often applied where systemic delivery of an active is desired, although it may also be useful for delivering an active to tissues underlying the skin with minimal systemic absorption.

"Transdermal application" as used herein includes administration through the skin. Transdermal application can be used for systemic delivery of an active agent; however, it is also useful for delivery of an active agent to tissues underlying the skin with minimal systemic absorption. In certain embodiments, "transdermal application" can also include epicutaneous application.

The term "hydrophobic compound" as used herein refers to pharmaceutically active ingredients (drugs, medicines or other agents) which are inherently hydrophobic, for example having a having a log P of at least 2 (Log P is the log of the octanol-water or buffer partition coefficient and can be determined by a variety of methods for those skilled in the art. The higher the value of log P, the greater the lipophilicity and thus lipid solubility of the chemical entity in question.)

The term "polar oil" as used herein refers to an oil compound comprising at least one polar group. Polar groups are known to those skilled in the art, may be ionic or non-ionic and include, but are not limited to, —COOH; —COO$^-$, —OH; and —NR$_1$R$_2$, with R$_1$ and R$_2$ representing H or a linear or branched C$_1$ to C$_{20}$ alkyl group.

The term "penetration enhancer" is a substance, compound or solvent that aids in the dissolution or dispersion of a cannabinoid in the compositions, and improves the rate of, or facilitates, for example, the percutaneous transport of an active agent across the skin for use and delivery of active agents to organisms such as mammals.

The term "oily vehicle" as used herein refers to a mixture of mono-, di- and triglycerides which aid in the solubility and bioavailability of cannabinoids in the compositions of the disclosure.

The term "cannabinoid" as used herein refers to any of the active compounds from the *Cannabis* plant, and includes, but is not limited to, the following substances: Δ-8-tetrahydrocannabinol, Δ-9- tetrahydrocannabinol (THC), cannabidiol (CBD), olivetol, cannabinol (CBN), cannabigerol (CBG), cannabichromene (CBC), Tetrahydrocannabivarin (THCV), Δ9-Tetrahydrocannabinol-C4 (THC-C4), nabilone, Δ-9-tetrahydro cannabinolic acid (THC-A), Cannabichromenic acid (CBC-A), Cannabigerolic acid (CBG-A) as well as the prodrugs and pharmaceutically acceptable salts of these cannabinoids.

The term "emollient" as used herein refers to a compound or mixture of compounds that adds or replaces natural oils in the skin, for example by maintaining the integrity of the hydrolipids of the skin.

The term "polar emollient" as used herein refers to emollient compounds, which are generally oils, having heteroatoms that differ in electronegativity. This results in a dipole moment. Typical polar oils are fatty alcohols, esters and triglycerides. While they are still water insoluble and oil-loving, these oils have unique characteristics due to their polar nature. They typically combine with higher HLB emulsifiers to make stable emulsions, they dissolve materials that are insoluble in nonpolar oils, and they provide unique properties when compared with nonpolar oils such as mineral oil.

The term "medium polar emollient" as used herein refers to as used herein refers to emollient compounds, which are generally oils, that are less polar than the polar emollients but still more polar than nonpolar oils such as mineral oil.

The term "humectant" as used herein refers to a compound or mixture of compounds intended to increase the water content of the top layers of skin.

The term "emulsifier" of "emulsifying agent" as used herein refers to a compound of mixture of compounds which promote or facilitate the dispersion of one substance in another to form an emulsion.

The term "terpene" as used herein includes both terpene hydrocarbons (derived from the five-carbon isoprene unit) and derivatives thereof, such as terpenoids, isoprenoids, sesquiterpene or triterpene, which may be considered as terpene hydrocarbons which have been modified by substitution or addition thereto of elements, or groups containing elements, such as oxygen, sulfur, nitrogen, halogens, etc. Unsaturated terpenes include, for example, alpha-pinene, beta-pinene, citral, humulene, caryophyllene, dipentene, terpinene, terpinolene, alloocimene, ocimene, alpha-pyronene, beta-pyronene, myrcene, philandrene, fenchene, sesquiterpenes, and the like; unsaturated terpene alcohols and phenols include alpha-terpineol, beta-terpineol, gamma-terpineol, terpinenol, eugenol, anethol and the like; other terpenes include unsaturated terpene esters, unsaturated terpene ethers and unsaturated polyterpenes. The terpenes can be found in natural butters, such as natural seed butters, or extracted as oils or extracts rich in terpenes, from plants, fruits, trees or other natural materials. Several non-limiting examples of terpenoids, classified based on the number of isoprene units that they contain, include: hemiterpenoids or hemiterpenes (1 isoprene unit); monoterpenoids or monoterpenes (2 isoprene units); sesquiterpenoids or sesquiterpenes (3 isoprene units); diterpenoids or diterpenes (4 isoprene units); sesterterpenoids or sesterterpenes (5 isoprene units); triterpenoids or triterpenes (6 isoprene units); sesquarterpenoids or sesquarterpenes (7 isoprene units); tetraterpenoids or tetraterpenes (8 isoprene units); and polyterpenoids or polyterpenes with a larger number of isoprene units (i.e. long chains of many isoprene units). Other terpenes includes limonene, myrcene, borneol, alpha- or beta-pinene, eucalyptol, terpineol, caryophyllene, camphene, alpha-bisabolol, delta-3-carene, farnesene.

The term "flavonoid compounds" as used herein refers to a class of plant secondary metabolites that have the general structure of a 15-carbon skeleton, which contains two phenyl rings (A and B) and heterocyclic ring (C). The basic chemical structure of a flavonoid as used herein is as follows:

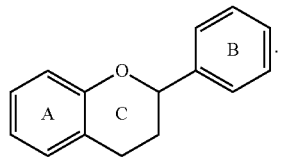

However, the term flavonoid includes the following flavonoids:

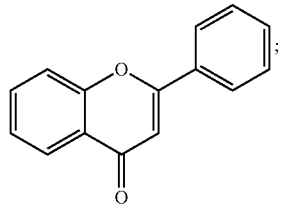 [SMILES: O=c1cc(-c2ccccc2)oc2ccccc12]

isoflavonoids:

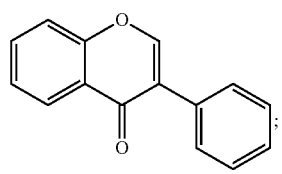 [SMILES: O=c1c(-c2ccccc2)coc2ccccc12]

and neoflavonoids:

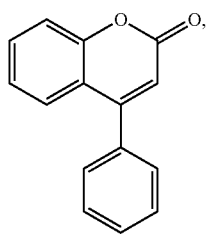 [SMILES: O=c1cc(-c2ccccc2)c2ccccc2o1]

as well as their non-ketone containing counterparts, know as flavanoids. Flavonoids are one of the largest known nutrient families, and include over 6,000 already-identified family members. Some of the best-known flavonoids include quercetin, kaempferol, catechins, and anthocyanidins. This nutrient group is most famous for its antioxidant and anti-inflammatory health benefits, as well as its contribution of vibrant color to foods.

The term "water" as used herein as an ingredient in the formulations of the application refers to pharmaceutically acceptable water.

The term "wt %" means a percentage expressed in terms of weight of the ingredient or agent over the total weight of the formulation multiplied by 100.

II. Formulations of the Application

In some embodiments, the present application includes a transdermal formulation comprising:

(a) an aqueous phase comprising water and at least one emulsion stabilizer;

(b) an oil phase comprising at least one emulsifier, at least one emulsion stabilizer, at least one emollient comprising at least one flavonoid, at least one other emollient, and a terpene-rich natural butter;

wherein the oil and aqueous phase form an emulsion;

(c) an external phase comprising at least one terpene-rich extract or oil, at least one penetration enhancer and a phospholipid-complexed flavonoid; and optionally (d) at least one preservative phase.

The terpene-rich transdermal formulations of the present application comprise an oil-in-water emulsion. In some embodiments, the formulation is a multiphase emulsion, such as an oil-in-water-oil emulsion or a water-in-oil-water emulsion.

In some embodiments, the aqueous phase comprises the water soluble emulsion stabilizer and the oil phase comprises the emulsifiers, the oil-soluble emulsion stabilizers, the polar and medium polar emollients, and the terpene-rich natural butter. In some embodiments both the oil phase and the aqueous phase comprise ingredients that are stable (i.e. do not degrade to a significant extent) at a temperature of about 65° C. to about 85° C., about 70° C. to about 80° C., or about 75° C., for a time period of about 30 minutes to about 12 hours, or about 1 hour to about 6 hours. In some embodiments, the external phase comprises at least one terpene-rich extract or oil.

Terpenes

In some embodiments, the transdermal formulations of the present application comprise terpenes from natural sources which act with the other components of the formulation to increase the effectiveness of the transdermal formulation and the administration of a hydrophobic active agent through the skin. In some embodiments, the active agent is a cannabinoid (such as nabilone), opioid (buprenorphine) or anesthetic (such as lidocaine) and the terpene-rich emulsion-based formulations potentiate the effect of the hydrophobic active agent. In some embodiments, the terpenes in combination with the other components of the formulation act synergistically to increase the effectiveness of the transdermal formulation and potentiate the effects of the hydrophobic agents.

In some embodiments, the oil phase comprises a terpene-rich natural butter, such as a seed butter, which contains terpenes (such as myrcene) having a similar profile to *Cannabis sativa*, and which can therefore act to potentiate the effects of the hydrophobic active agents, such as tetrahydrocannabinol (THC) and the structurally similar non-psychoactive cannabidiol (CBD). In one embodiment, the terpene-rich natural butter is mango butter.

In some embodiments, the natural butter is present in the formulations of the application in an amount of about 1 wt % to about 10 wt %, about 2 wt % to about 5 wt %, or about 3 wt %.

In some embodiments, the external phase comprises at least one terpene-rich extract or oil from natural sources, such as essential oils, which also act to potentiate the transdermal effects of the hydrophobic active agents. In some embodiments, the terpene-rich extracts or oils contain high concentrations of terpenes, and includes extracts and/or oils from mango (for example, Mangifera Indica fruit extract), hops (Humulus lupulus extract), clove oil (Eugenia Caryophyllus Bud oil), myrtle lemon (Backhousia Citridora Leaf oil), black pepper (Piper Nigrum Seed oil) or fennel (Foeniculum Vulgare oil), or any other source of terpenes or terpenoids.

In some embodiments, the terpene-rich extracts or oils from natural sources are present in the formulations of the application in an amount of about (in total) 0.1 wt % to about 10 wt %, or about 0.2 wt % to about 5 wt % (in total). In some embodiments, each terpene-rich extract or oil is present in an amount of less than about 5 wt %, or less than about 2 wt %.

In some embodiments, the terpene-rich formulations act synergistically with the other components of the emulsion based formulation to increase the transdermal delivery of the hydrophobic active agents through the skin. In some embodiments, the terpene-rich emulsion-based formulations effectively deliver hydrophobic active agents through the skin without depot.

Emulsifiers

In some embodiments of the present application, the emulsifier is any oil-soluble fatty acid ester or mixture of fatty acid esters in which the fatty acid esters have a fatty acid composition similar to the fatty acid composition of skin for generating skin-compatible liquid crystals and to mimic the molecular organization of the intracellular lipidic laminae of the stratum corneum. Such liquid crystals are able to rapidly cross skin layers as well as to integrate into the skin's own lipid barrier to provide strength and greater integrity to this barrier.

In some embodiments the fatty acid esters are selected from sugar alcohol and fatty acid alcohol esters of any $C_{14}$-$C_{26}$-fatty acid or mixtures thereof. In some embodiments, the fatty acid esters are esters of fatty acids that are present in olive oil, palm oil and/or canola oil. In some embodiments, the fatty acids are esterified with fatty acid alcohols such as, but not limited to, cetyl alcohol, cetaryl alcohol, lauryl alcohol, steelyl alchololl, myristyl alcohol and/or oleyl alcohol. In some embodiments, the fatty acids are esterified with sugar alcohols such as, but not limited to, sorbitol, glycerol, mannitol, inositol, xylitol, erythritol, threitol, arabitol and/or ribitol. Olive oil fatty acid esters, and their use in transdermal formulations is described, for example, in U.S. Patent Application Publication No. 2011/0021439. In some embodiments, the fatty acid esters are sorbitan esters of palm oil or olive oil, such as sorbitan olivate or sorbitan palmitate. For example, sorbitan olivate is derived from fatty acids present in olive oil and esterified with sorbitol, and sorbitan palmitate is derived from fatty acids present in palm oil and esterified with sorbitol. In other embodiments, the fatty acid esters are cetearyl esters of olive oil, such as cetearyl olivate. For example, cetearyl olivate is derived from fatty acids present in olive oil and esterified with cetearyl alcohol. In further embodiments, the fatty acid esters are cetyl esters of palm oil, such as cetyl palmitate. For example, cetyl palmitate is derived from fatty acid esters present in palm oil and esterified with cetyl alcohol.

In some embodiments, the emulsifier is present in the formulations of the application in an amount of about 1 wt % to about 10 wt %, about 2 wt % to about 8 wt %, or about 4 wt % to about 6 wt %.

In other embodiments, the formulations may also contain an anionic, oil-in-water emulsifier, such as sodium stearoyl glutamate. In some embodiments, the anionic emulsifier is present in an amount of about 0.1 wt % to about 1 wt %, or about 0.5 wt % to about 0.8 wt %.

Emulsion Stabilizers

In some embodiments, the emulsion stabilizer is any compound or mixture of compounds that helps to maintain the oil-in-water emulsion. There are three types of emulsion instability: flocculation, creaming, and coalescence. Flocculation describes the process by which the dispersed phase comes out of suspension in flakes. Coalescence is another form of instability, which describes when small droplets combine to form progressively larger ones. Emulsions can also undergo creaming, which is the migration of one of the substances to the top or bottom (depending on the relative densities of the two phases) of the emulsion under the influence of buoyancy or centripetal force when a centrifuge is used. Generally, emulsion stability refers to the ability of an emulsion to resist change in its properties over time. In the present application an emulsion stabilizer is present in both the oil phase and the aqueous phase.

In some embodiments, the emulsion stabilizer is one or more waxes. In some embodiments the waxes are selected from animal and plant waxes and mixtures thereof. In some embodiments, the plant wax is a wax derived from olives or from palm (e.g. carnauba wax). In some embodiment, the animal wax is beeswax. The one or more waxes are stabilizers that are present in the oil phase of the formulation.

In some embodiment, the oil phase emulsion stabilizer, if present, is present in the formulation in an amount of about 1 wt % to about 10 wt %, about 2 wt % to about 8 wt % or about 3 wt % to about 6 wt %.

In some embodiments, the emulsion stabilizer is one or more thickening agents. In some embodiments, the thickening agents are any compound or mixture of compounds that maintains components in the formulation in suspension and provides a suitable consistency to the formulation.

In some embodiments, the emulsion stabilizer is selected from natural polymers, gums and synthetic polymers, and mixtures thereof. In some embodiments, natural polymers, gums and synthetic polymers, and mixtures thereof, are water soluble and therefore are present in the aqueous phase of the formulation. In some embodiments, the natural polymers are selected from alginic acid and derivatives thereof, cellulose and derivatives thereof and scleroglucans, and mixtures thereof. In some embodiments, the gums are selected from xanthan gum, tara gum, guar gum and arabic gum, and mixtures thereof. In some embodiments, the synthetic polymers are selected from polyacrylates, polyisobutenes and polysorbates, and mixtures thereof.

In some embodiments, the aqueous phase emulsion stabilizer is present in the formulations of the application in an amount of about 0.1 wt % to about 1 wt %, about 0.2 wt % to about 0.8 wt %, or about 0.4 wt % to about 0.6 wt %.

Emollient Comprising at Least One Flavonoid

In some embodiments, the one or more emollients comprising one or more flavonoid compounds are polar emollients. Polar emollients generally include natural oils and extracts from plants. In some embodiments, the polar emollients are derived from fruits (including berries), vegetables, herbs, spices, legumes, leaves, seeds and/or grains. In some embodiments, the polar emollient is a natural oil or extract from *citrus, Ginkgo biloba*, tea, wine, cacao, onion, kale, parsley, red beans, broccoli, endive, celery, cranberries, blackberries, red raspberries, blackcurrants (Ribes Nigrum seed oil), acai, blueberries, bilberries, milk thistle, apples, hawthorn, *Echinacea*, grapes, and/or soy. In some embodiments, the polar emollient is emu oil.

In some embodiments, the polar emollient comprising one or more flavonoid compounds is a natural oil or extract from the genera *Rubus, Ribes, Argania, Nymphaea, Peucedanum* or *Imperatoria, Sambucus, Calendula, Butea, Citrus* (e.g. lime), or species or subspecies thereof. In some embodiments, the polar emollient comprising one or more flavonoid compounds comprises Leptospermum Scoparium and/or manuka oil. In some embodiments, the polar emollient comprising one or more flavonoid compounds comprises Argan oil, Sea buckthorn oil, Cicatrol, Protectol, and/or Calendula.

In some embodiments, the emollients comprising one or more flavonoid compounds are present in the formulations of the application in an amount of about 1 wt % to about 20 wt %, about 3 wt % to about 15 wt %, or about 5 wt % to about 12 wt %.

Further Emollients

The polarity of the emollients used in the present can vary depending on the identity of the emulsifiers and emulsion stabilizers, however can nonetheless be selected by a person skilled in the art. In some embodiments, the formulations of the present application comprise both polar emollients and medium polar emollients.

In some embodiments, further polar emollients used in the present application comprise an oil from an animal in the family Dromaius, for example Dromiceius (emu) or a plant, such as, Jojoba oil, Olive oil, hemp and/or coconut oil.

In some embodiments the one or more further polar emollients are present in an amount of about 1% wt % to about 10 wt %, about 3 wt % to about 7 wt %, or about 4 wt % to about 8 wt %.

In some embodiments, the medium polar emollient is an ester such as octyl palmitate, isopropyl stearate and isopropyl palmitate, or an alcohol such as octyl dodecanol, or mixtures thereof.

In some embodiments the emollients also act as a thickener (stabilizer) and/or a humectant.

In some embodiments, the one or more medium polar emollients are present in an amount of about 1% wt % to about 10 wt %, about 3 wt % to about 7 wt %, or about 3 wt % to about 5 wt %.

Flavonoid-Containing Extract

In some embodiments, one or more flavonoid-containing extracts may be present in the external phase and is any suitable water soluble natural extract comprising a flavonoid with anti-inflammatory and/or antioxidant properties. In some embodiments, the one or more flavonoid-containing extracts are plant-based extracts, including but not limited to, one or more of *Nymphaea caerulea* flower extract, *Peucedanum ostruthium* leaf extract, *Sambuscus nigra* extract, *Calendula* flower Extract, *Gingko biloba* extract, *Imperatoria Alpaflor* extract, Sambucus Alpaflor extract, Blue lotus extract, *Calendula Alpaflor* extract, Masterwort extract, Elderberry extract, Angelica extract, green tea extract, chamomile extract, pomegranate pericarp and *Peucedanum ostruthium* leaf extract.

In some embodiments, the one or more flavonoid-containing extracts for the external phase are present in an amount of about 1% wt % to about 15 wt %, about 3 wt % to about 10 wt %, or about 4 wt % to about 8 wt %.

Penetration Enhancer

Ideally, penetration enhancers reversibly reduce the barrier resistance of the stratum corneum without damaging viable cells.

In some embodiments the penetration enhancer is selected from ethoxydiglycol (transcutanol) and mixtures thereof, and may be present in an amount of about 1% wt % to about 5 wt %, about 1 wt % to about 2 wt %, or about 1.5 wt %.

Phospholipid-Complexed Flavonoid

In some embodiments, the flavonoid is a bioflavonoid isolated from plants such as, but not limited to, *Gingko bilboa, Crataegus* sp., *Passiflora incarnate, Tormentilla potentilla, Tea sinensis., Aurantium* sp., *Citrus* sp., *Eucaliptus* sp., *Matricaria chamomilla, Rheum* sp. and *Fagara sylanthoides*. In some embodiments, the flavonoid is isolated from green tea, buckwheat, the leaves and petioles of asparagus, fruit of the Fava D-Ante tree, fruits and fruit rinds, for example from *citrus* fruits such as orange, grapefruit, lemon and lime, and berries such as mulberries and cranberries. In some embodiments, the flavonoid is selected from quercetin, myrcetin, apigenin and rutin, and mixtures thereof.

In some embodiments, the phospholipid is any phospholipid, or mixture of phospholipids, from a plant or animal, or any synthetic phospholipid. In some embodiments, the phospholipid is selected from a phosphatidylcholine, a phosphatidylethanolamine, phosphatidylinostinol and phosphatidylserine, and mixtures thereof.

In some embodiments, the phospholipid-complexed flavonoid is commercially available. In some embodiments, the phospholipid-complexed flavonoid is prepared by combining the phospholipid and flavonoid in a suitable solvent or mixture of solvents, in a mole ratio of phospholipid:flavonoid of about 0.5 to 2, or about 1, and isolating the resulting complex, for example, but removal of the solvent(s), precipitation and/or lyophilization.

In some embodiments, the phospholipid-complexed flavonoid is present in an amount of about 0.5% wt % to about 5 wt %, about 1 wt % to about 4 wt %, or about 1.5 wt % to about 2.5 wt %.

Complexes of bioflavonoids with phospholipids, their preparation and use, are described, for example in U.S. Pat. No. 5,043,323, the contents of which are incorporated by reference in their entirety.

Water

The balance of the aqueous phase of the composition is made up of water. Further, it is an embodiment that the solvent for the external phase and/or the preservative phase (if present) comprises water. In some embodiments, the water is purified and/or demineralized water. The purified water may, for example, be filtered or sterilized.

In some embodiments, the amount of water in the aqueous phase is about 40 wt % to about 60 wt %, or about 45 wt % to about 60 wt %, or about 58.5 wt % (based on the total weight of the formulation).

In some embodiments, the amount of water in the external phase is about 0.5 wt % to about 5 wt %, or about 1 wt % to about 3 wt % (based on the total weight of the formulation).

In some embodiments, the amount of water in the preservative phase (if present) is about 0 wt % to about 5 wt %, (based on the total weight of the formulation).

Preservatives

In some embodiments, the formulations of the present application comprise at least one preservative. Preservatives include antimicrobial agents. In some embodiments the preservatives prevent or inhibit the growth of micro-organisms, including bacteria, yeasts and molds. In some embodiments, the preservatives prevent or inhibit undersirable chemical reactions from occurring.

In some embodiments, the preservative comprises a preservative system comprising phenoxyethanol, benzoic acid, and dehydroacetic acid. In some embodiments, the preservative is sodium levulinate and potassium sorbate. In some embodiments, the preservative comprises capryl glycol, which also advantageously has humectant and emollient properties. In some embodiments, the preservative comprises chlorphensin. In some embodiments, the preservative comprises ethylhexylglycerin which also advantageously has skin conditioning and emollient properties and acts as a deodorant. In some embodiments, the preservative comprises a natural antimicrobial agent (antibacterial, antifungal, antiviral). In some embodiments, the natural antimicrobial agent is selected from tea tree oil (*Malaleuca alternifolia* leaf oil) and myrtyl lemon essential oil. In some embodiments, the preservative comprises a preservative and a preservative booster.

In some embodiments, other components of the formulation have intrinsic anti-microbial properties.

In some embodiments, the one or more preservatives are present in an amount of about 0% wt % to about 5 wt %, about 1 wt % to about 4 wt %, or about 1.5 wt % to about 3 wt %.

Further Optional Ingredients

In some embodiments, the formulations of the present application further comprise additional ingredients that are common in the transdermal base formulation art. These ingredients are, for example, but not limited to, active pharmaceutical ingredients, pH adjusters or buffering agents, further solvents, solubilizers, chelating agents, pigments, fragrances, humectants and/or solubilizers.

(a) pH Adjusters/Buffering Agents

In some embodiments, the formulations of the application further comprise one or more pH adjusters, such as acidic, basic, or buffering components such as disodium phosphate. These components may be added to provide the optimal pH balance for the skin. They may also be added to provide an optimal pH for one or more the components of the formulation.

In some embodiments, the pH adjuster is selected from sodium hydroxide and potassium citrate. In some embodiment, the one or more pH adjusters are present in the formulation in an amount of about 0.05% wt % to about 2.0% wt, about 0.1 wt % to about 1.0 wt %, or about 0.8 wt % to about 0.8 wt %.

In some embodiments, the one or more pH adjusters are in the aqueous phase or the external phase.

(b) Chelating Agents

In some embodiments, the formulations of the application further comprise one or more chelating agents. In some embodiments, the chelating agents bind to metals which can inhibit the activity of the antimicrobial preservatives. In some embodiments, the chelating agent is sodium phytate or ethylendiamine tetraacetic acid (EDTA). In some embodiments, the one or more chelating agents are present in the formulation in an amount of about 0.01% wt % to about 0.2% wt, about 0.02 wt % to about 0.1 wt %, or about 0.03 wt % to about 0.05 wt %.

In some embodiments, the one or more chelating agents are in the aqueous phase or the external phase.

(c) Humectants

In some embodiments, the formulations of the present application further include one or more humectants. In some embodiments, the one or more humectants include, but are not limited to, glycerine (which also acts as a and additional solvent).

In some embodiments, the one or more humectants are present in the formulation in an amount of about 0.5 wt % to about 10% wt, about 1 wt % to about 7 wt %, or about 2 wt % to about 5 wt %.

In some embodiments, the one or more humectants are in the aqueous phase.

(d) Solubilizers

In some embodiments, the formulations of the present application further include one or more solubilizers. In some embodiments, the one or more solubilizers include, but are not limited to, inulin lauryl carbamate.

In some embodiments, the one or more solubilizers are present in the formulation in an amount of about 0.01 wt % to about 5% wt, about 0.1 wt % to about 2 wt %, or about 0.2 wt % to about 1 wt %.

In some embodiments, the one or more solubilizers are in the external phase.

(e) Active Pharmaceutical Ingredients

The formulations of the present disclosure may further comprise a hydrophobic agent, such as pharmaceutical active agent or other natural product active ingredient, such as a cannabinoid, opioid or anesthetic, which when combined with the terpene-rich formulation is suitable for the transdermal delivery of the agent into the dermis. In one embodiment, the active agent is derived from *Cannabis*.

In some embodiments, there is included a topical therapeutic formulation comprising one or more hydrophobic active pharmacological ingredients (APIs). As used herein, API may include active molecules derived from natural, synthetic or semi-synthetic means, as well as other active ingredients, such as extracts from *Cannabis* plants.

In some embodiments, the active pharmaceutical ingredient (API) is solubilised or dispersed in an effective amount of a suitable vehicle (e.g. solvent(s) or diluent(s)). A skilled person can readily determine which solvents or diluents will be appropriate for a particular API. In some embodiments, the API is included in the external phase. In some embodiments, the API is included in an amount of about 0.01 wt % to about 1 wt %, about 0.05 wt % to about 0.5 wt %, or about 0.075 wt %.

In one embodiment, the active pharmaceutical ingredient is present in the external phase and is nabilone. In one embodiment, the nabilone is present in an amount of about 0.01 wt % to about 1 wt %, about 0.05 wt % to about 0.5 wt %, or about 0.05 wt %.

In another embodiment, the active pharmaceutical ingredient is present in the external phase and is buprenorphine. In one embodiment, the buprenorphine is present in an amount of about 0.001 wt % to about 1 wt %, about 0.01 wt % to about 0.05 wt %, or about 0.02 wt %.

In another embodiment, the active pharmaceutical ingredient is present in the external phase and is an anesthetic, for example, a topical anesthetic. In another embodiment, the anesthetic is bupivacaine or lidocaine. In another embodiment, the anesthetic is a combination of bupivacaine, lidocaine and epinephrine. In one embodiment, the bupivacaine is present (as hydrochloride) in an amount of about 0.1 wt % to about 5 wt %, about 1.0 wt % to about 3.0 wt %, or about 2.0 wt %. In one embodiment, the lidocaine is present in an amount of about 0.1 wt % to about 10 wt %, about 2.0 wt % to about 8.0 wt %, or about 5.0 wt %. In one embodiment, the epinephrine is present in an amount of about 0.001 wt % to about 1 wt %, about 0.01 wt % to about 0.05 wt %, or about 0.05 wt %.

In another embodiment, the active pharmaceutical ingredient is present in the external phase and is a synthetic cannabinoid, for example, synthetic THC. In one embodiment, the synthetic cannabinoid is present in an amount of about 0.1 wt % to about 5 wt %, about 1.0 wt % to about 3.0 wt %, or about 1.5 wt %.

In another embodiment, the active pharmaceutical ingredient is present in the external phase and is a plant-derived cannabinoid, for example, THC and/or CBD. In one embodiment, the active pharmaceutical ingredient is a combination of THC and CBD and is present at a ratio of between about 0.1:5.0 to 5.0:0.1, or about 1:1. In one embodiment, the plant-derived cannabinoid is present in an amount of about 0.1 wt % to about 5 wt %, about 1.0 wt % to about 3.0 wt %, or about 1.0 wt %.

In some embodiments, the present application includes a method for the transdermal administration of one or more API's comprising administering an effecting amount of one or more of the formulations of the present application to a subject in need thereof, wherein the one or more formulations comprise the API. In further embodiments, the present application includes a use of one or more formulations of the present application for the administration of one or more API's to a subject, wherein the one or more formulations comprise the API. In some embodiments, the terpene-rich formulation potentiates the effect of the hydrophobic API.

In one embodiment, in addition to using the cream in medical wound care facilities, it can also be used in the field by nurses, i.e., during home visits or in wound centers when wounds care requires sharp or surgical debridement. It can also be used in other procedures requiring topical local anesthetic, for example, during venipuncture to anesthetize the site of blood collection or IV insertion. In another embodiment, the formulation is useful for dental applications as an oral local anesthetic.

III. Additional Formulations of the Application

The present application also relates to formulations comprising a polar oil, an oily vehicle and an active ingredient comprising a hydrophobic compound, such as cannabinoids and/or terpenes.

The present disclosure includes formulations (such as transdermal or oral (buccal) formulations) containing hydrophobic compounds, wherein the formulations comprise an oily vehicle which aids in the solubility and bioavailability of the hydrophobic compound.

In one embodiment, the hydrophobic compound is a cannabinoid.

In another embodiment, the hydrophobic compound is a terpene, such as a sesquiterpene or triterpene. Several non-limiting examples of terpenoids, classified based on the number of isoprene units that they contain, include: hemiterpenoids or hemiterpenes (1 isoprene unit); monoterpenoids or monoterpenes (2 isoprene units); sesquiterpenoids or sesquiterpenes (3 isoprene units); diterpenoids or diterpenes (4 isoprene units); sesterterpenoids or sesterterpenes (5 isoprene units); triterpenoids or triterpenes (6 isoprene units); sesquarterpenoids or sesquarterpenes (7 isoprene units); tetraterpenoids or tetraterpenes (8 isoprene units); and polyterpenoids or polyterpenes with a larger number of isoprene units (i.e. long chains of many isoprene units). In one embodiment, the terpene is limonene, myrcene, borneol, alpha- or beta-pinene, eucalyptol, terpineol, caryophyllene, camphene, alpha-bisabolol, delta-3-carene, farnesene, The present disclosure includes formulations (such as transdermal or oral (buccal) formulations) containing hydrophobic compounds, wherein the formulations comprise an oily vehicle which aids in the solubility and bioavailability of the compound. Accordingly, in one embodiment of the disclosure, there is also included a formulation comprising:

i) at least one polar oil;

ii) an oily vehicle comprising mono-, di- and triglycerides;

iii) a penetration enhancer; and iv) an active ingredient comprising a hydrophobic compound.

In one embodiment, the active ingredient comprising a hydrophobic compound is soluble in a polar oil, such as a cannabinoid extract or terpene extract.

In one embodiment, the formulations comprise at least one polar oil which helps to solubilize and dilute the hydrophobic compound in the formulation. In one embodiment, the polar oil acts as a carrier oil, and helps to stabilize the formulation. In one embodiment, the polar oil comprises a fatty acid, such as an unsaturated or saturated fatty acid. In one embodiment, the unsaturated fatty acid is oleic acid, linoleic acid, myristoleic acid, palmitoleic acid, sapienic acid, elaidic acid, vaccenic acid, linoelaidic acid, α-linoleic acid, arachidonic acid, eicosapentaenoic acid, erucic acid, or docosahexaenoic acid, and stereoisomers thereof. In another embodiment, the saturated fatty acid is caprylic acid, capric acid, lauric acid, myristic acid, palmitic acid, stearic acid, arachidic acid, behenic acid, lignoceric acid, or cerotic acid, and stereoisomers thereof.

In another embodiment, the term polar oil refers to classes of oils that contain, for example, combinations of the specific oils recited above. For example, vegetable oils, nut oils and animal oils may comprise combinations of the fatty acids listed above. In one embodiment, the at least one polar oil is argan oil, sunflower oil, olive oil, avocado oil or jojoba oil. In one embodiment, the polar oil is argan oil.

In another embodiment, the formulations comprise an oily vehicle comprised of mono-, di- and tri-glycerides. In one embodiment, the oily vehicle further helps to solubilize the hydrophobic compound in the formulation. In another embodiment, the oily vehicle comprises mono-, di- and tri-glycerides of saturated and/or unsaturated fatty acids having a hydrocarbon chain between 6 and 20 carbon atoms. In one embodiment, the fatty acid is derived from a vegetable source, such as corn oil, canola oil, olive oil etc. In another embodiment, the unsaturated fatty acid is oleic acid, linoleic acid, stearidonic acid, eicospentaenoic acid, docosahexaenoic acid, arachidonic acid etc. In one embodiment, the fatty acid is oleic acid and/or linoleic acid.

In another embodiment, the oily vehicle is a mixture of mono-, di- and triglycerides of oleic acid and linoleic acid. In one embodiment, the oily vehicle is obtained by alcoholysis between glycerol and refined corn oil, followed by winterization to remove saturated mono-, di- and triglycerides. In one embodiment, the oily vehicle comprises
   i) about 25-75% (or about 32-52%) of monoglycerides of oleic and linoleic acid;
   ii) about 25-75% (or about 40-55%) of diglycerides of oleic and linoleic acid; and
   iii) about 1-50% (or about 5-20%) of triglycerides of oleic and linoleic acid In one embodiment, the cannabinoid is any compound isolated from the *Cannabis* plant which is capable of treating one or more cannabinoid-responsive diseases or conditions. In particular embodiments, the cannabinoid is cannabidiol (CBD) or (-)-trans-$\Delta^9$-tetrahydrocannabinol (THC) or mixtures thereof. In one embodiment, the cannabinoid is THC.

In another embodiment, the formulations contain a penetration enhancer which aid in the bioavailability of the solubilized hydrophobic compound. Without solubilization of the hydrophobic compound in the formulation, the hydrophobic compound will not be absorbed through the skin or oral cavity. In one embodiment, the penetration enhancer is a glycol. In one embodiment, the penetration enhancer is ethoxy diglycol. In other embodiments, the penetration enhancer is dimethyl isosorbide, or mixtures of glycols (such as ethoxy diglycol) and dimethyl isosorbide. In one embodiment, the penetration enhancer is 2-(2-Ethoxyethoxy)ethanol, for example, Transcutol® CG.

In one embodiment, the formulations of the present disclosure are transparent liquids at room temperature. In another embodiment, the components of the formulation act to first solubilize the active ingredient comprising a hydrophobic compound in the formulation, followed by enhancing the penetration of the hydrophobic compound through the skin or oral cavity.

In another embodiment, the formulations of the present disclosure further include flavonoid compounds. The term "flavonoid compounds" as used herein refers to a class of plant secondary metabolites that have the general structure of a 15-carbon skeleton, which contains two phenyl rings (A and B) and heterocyclic ring (C). The basic chemical structure of a flavonoid as used herein is as follows:

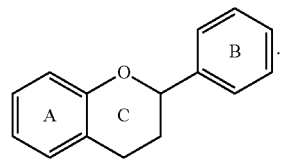

However, the term flavonoid includes the following flavonoids:

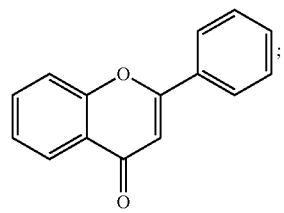 [SMILES: O=c1cc(-c2ccccc2)oc2ccccc12]

isoflavonoids:

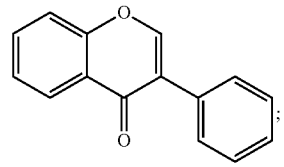 [SMILES: O=c1c(-c2ccccc2)coc2ccccc12]

and neoflavonoids:

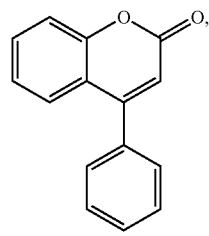 [SMILES: O=c1cc(-c2ccccc2)c2ccccc2o1]

as well as their non-ketone containing counterparts, known as flavanoids. Flavonoids are one of the largest known nutrient families, and include over 6,000 already-identified family members. Some of the best-known flavonoids include rutin, quercetin, kaempferol, catechins, and anthocyanidins. This nutrient group is most famous for its antioxidant and anti-inflammatory health benefits, as well as its contribution of vibrant color to foods. Other flavonoids includes those present in, for example, peppermint oil, such as eriocitrin, hesperidin etc.

In another embodiment of the disclosure, the active ingredient comprising a cannabinoid is extracted from a plant in the Cannabaceae family, for example using carbon dioxide ($CO_2$). In some embodiments, $CO_2$ extraction of cannabinoids results in higher amounts of cannabinoids being extracted from the plant, resulting in a viscous oil containing the cannabinoids.

In another embodiment, the disclosure includes formulations comprising:

i) an active ingredient comprising a cannabinoid or terpene, wherein the cannabinoid is $CO_2$ extracted, in an amount between about 5-10% (w/w), or about 6.6%;

ii) an oily vehicle comprising mono-, di- and triglycerides in an amount between about 20%-60%, or about 40.0%;

iii) a polar oil (such as argan oil), present in an amount between about 25%-50%, or about 33.4%; and iv) a penetration enhancer (such as Transcutol® CG) present in an amount between about 10%-30%, or about 20.0%.

III. Processes of the Application

In some embodiments, the present application includes a process for preparing a transdermal delivery base formulation as described herein comprising:

(a) heating an aqueous phase comprising water and at least one emulsion stabilizer to a first temperature;
(b) heating an oil phase comprising at least one emulsifier, at least one emulsion stabilizer, at least one emollient comprising at least one flavonoid, at least one other emollient, and a terpene-rich natural butter to the first temperature;
(c) adding the aqueous phase to the oil phase with stirring at the first temperature and continuing to stir at the first temperature until an emulsion is formed;
(d) cooling the emulsion in (c) to a second temperature; and, in any order:
(e) adding one or more external phases comprising at least one penetration enhancer, at least one terpene-rich extract or oil, and a phospholipid-complexed flavonoid to the emulsion at the second temperature; and optionally
(f) adding one or more preservative phases to the emulsion.

In some embodiments, the first temperature is about 65° C. to about 85° C., about 70° C. to about 80° C., or about 75° C.

In some embodiments, the second temperature is about 30° C. to about 50° C., about 35° C. to about 45° C., or about 40° C.

In some embodiments, the process further comprises preparing the external phase wherein the phospholipid-complexed flavonoid is stirred with water for a sufficient amount of time to become hydrated prior to being combined with the remaining ingredients for the external phase.

In some embodiments, the phases and emulsions are mixed with an homogenizer prior to combining with other phases.

In other embodiments, the present application includes a process for preparing a transdermal terpene-rich delivery formulation as described herein comprising:

(a) heating an aqueous phase comprising water in a first vessel. In some embodiments, the aqueous phase is heated to a temperature of about 65° C. to about 85° C., about 70° C. to about 80° C., or about 75° C.
(b) mixing a humectant and at least one emulsion stabilizer, for example, a thickener, in a vessel for a time sufficient to obtain a homogenous mixture. After a homogenous mixture is obtained, the mixture is added to the first vessel of part (a).
(c) heating an oil phase comprising at least one emulsifier, at least one emulsion stabilizer, at least one emollient comprising at least one flavonoid, terpene-rich natural butter and at least one other emollient in a vessel for a time sufficient to obtain a homogenous mixture. In some embodiments, the oil phase is heated to a temperature of about 65° C. to about 85° C., about 70° C. to about 80° C., or about 75° C. After a homogenous mixture is obtained, the oil phase is added to the first vessel containing (a) and (b), and the mixture is stirred for a time to complete emulsification, for example, about 1-10 minutes, or about 2-5 minutes, or about 2-3 minutes, to obtain an emulsion.
(d) the emulsion from (c) is cooled, optionally while stirring. In some embodiments, the emulsion is cooled to about 30° C. to about 50° C., about 35° C. to about 45° C., or about 40° C.
(f) the external phases are then added to the emulsion in the first vessel at the same temperature (about 30° C. to about 50° C., about 35° C. to about 45° C., or about 40° C.):
   at least one terpene fruit or plant extract and a penetration enhancer are added to the emulsion and mixed until homogeneous;
   at least one terpene essential oil and a thickening agent are mixed in a separate vessel until homogenous and then added to the emulsion and mixed until homogeneous;
   optionally, a preservative phase is mixed one by one into the emulsion and mixed until homogeneous;
   in a separate vessel, water (for example, demineralized water) and a phospholipid-complexed flavonoid is mixed until a homogenous solution is obtained, and subsequently mixed with the emulsion. In some embodiments, the phospholipid-complexed flavonoid is stirred with the water for a sufficient amount of time to become hydrated prior to being combined with the remaining ingredients.
(g) optionally, the final homogenous solution is cooled to room temperature.

In some embodiments, the phases and emulsions are mixed with an homogenizer prior to combining with other phases.

IV. Methods of Administration

In some embodiments, the present application includes a method for the transdermal or buccal administration of hydrophobic compounds comprising administering an effective amount of one or more of the formulations of the present application to a subject in need thereof. In further embodiments, the present application includes a use of one or more formulations of the present application for the administration of a hydrophobic compound to a subject.

The present application includes therapeutic methods and uses of the formulations described herein. In some embodiments, the formulations are used in methods to treat one or more cannabinoid-responsive diseases and conditions.

Accordingly, the present application includes methods for treating one or more cannabinoid-responsive diseases and conditions, comprising administering an effective amount of a transdermal formulation of the application to a subject in need thereof. Also included is a use of a transdermal formulation of the application to treat one or more cannabinoid-responsive diseases and conditions.

In some embodiments, the cannabinoid-responsive disease and condition is selected from one or more of pain, such as chronic pain, acute pain, neuropathic pain; epilepsy; pain related to chemotherapy; treatment of side effects due to chemotherapy such as nausea and vomiting. In another embodiment, the cannabinoid-responsive disease and condition is a neurological disorder, such as epilepsy or epilepsy related symptoms.

In some embodiments, the formulations of the application are used in conjunction with other therapies to treat cannabinoid-responsive diseases and conditions.

In other embodiments of the disclosure, the formulations are administered in the form of a buccal or oral spray, in which the spray optionally provides a metered dose of the active ingredient in the formulation to the oral or buccal cavity. In one embodiment, the formulations comprising the oily vehicle are formulated for oral or buccal sprays.

In further embodiments, the formulations are administered as a vape in a vaporizer, wherein the subject inhales the vapors of the formulation.

In further embodiments, the formulations are formulated as soft gel caps for oral delivery of the cannabinoid. For example, the formulations of the disclosure are contained within a capsule formed predominantly of gelatin, glycerine, and water for oral administration of the formulation.

In another embodiment, the formulations are formulated for sub-lingual administration, such as drops, or sprays, wherein the cannabinoid formulation diffuses through the membranes beneath the tongue. In another embodiment, the formulations of the present disclosure are formulated as bio-films or sublingual strips which melt within the mouth such that the formulation diffuses through the membranes under the tongue.

In further embodiments, the formulations are included in foodstuffs in which the cannabinoid is administered in the foodstuff when the subject consumes the food.

EXAMPLES

The following non-limiting examples are illustrative of the present application:

Example 1

A Topical Cannabinoid Base Formulation 1

A topical cannabinoid base formulation was prepared using the ingredients listed in Table 1.
Procedure for Making Formulation 1.

Step A: Demineralized water was added to a master kettle and heated to 75° C.

Step B: In a separate vessel, humectant (glycerin) and thickener (xanthan gum) were mixed until homogenous and added to the master kettle in Step A.

Step C: In another kettle, ingredients of phase A were combined and heated to 75° C. Phase A included cetearyl olivate, sorbitan olivate, cetyl palmitate, sorbitan palmitate, sorbitan olivate, sodium stearoyl glutamate, Mangifera Indica seed butter, *Cannabis sativa* seed oil, blackcurrant seed oil, and isopropyl palmitate.

Step D: the ingredients of phase A were mixed into the master kettle with stirring until emulsion was formed, about 2-3 minutes.

Step E: The solution mixture in the master kettle was gradually cooled, while stirring. When the reaction temperature reached 35-40° C., ingredients of phase C were added one by one, whereby with each addition the solution was mixed until homogenous. Phase C included phenoxyethanol, benzoic acid, dehydroacetic acid, sodium levulinate and potassium sorbate.

Step F: the ingredients of phase D were added one by one, whereby with each addition the solution was mixed until homogenous. Phase D included Mangifera Indica fruit extract, ethoxydiglycol and Humulus lupulus extract.

Step G: In a separate vessel, the components of Phase E, were added and mixed. Once a homogenous solution was achieved, the solution mixture was added into the master kettle, followed by stirring until the solution became homogenous. Phase E included polyacrylate-13, polyisobutene, polysorbate 20, clove oil, myrtle lemon oil, black pepper oil and fennel oil.

Step F: In a separate vessel, phospholipid complexed rutin was mixed with demineralized water. The homogenous solution was then added to the master kettle and the final formulation cooled.

Step F: The viscosity using a Brookfield RVT, T4, 30 RPM instrument and pH measurements of the final solution were taken. The viscosity and pH values should be within the range of 150,000 +/−30,000 cps and 5.0-6.0 at 25° C., respectively. The formulation was a light yellow-beige cream.

Example 2

Nabilone 0.05% in Cannabinoid Base

To the formulation of Example 1, was added Nabilone in the external phase (0.05% wt; from 0.5% formulation having 0.1% nabilone in carrier), phosphatidylcholine (1.0% wt), and ethoxydiglycol (1.0% wt) and 97.5% wt of the formulation of Example 1.

Example 3

Buprenorphine 0.02% in Cannabinoid Base

To the formulation of Example 1, was added Buprenorphine in the external phase (0.11% of a buprenorphine solution to total 0.02% wt buprenorphine), phosphatidylcholine (0.5% wt) and lysophospholipid (0.5% wt) and 98.89% wt of the formulation of Example 1.

Example 4

Treatment of Neuralgia using Buprenorphine Formulation 51 year female suffering with Trigemminal Neuralgia in the maxillary of the face. 0.5 gram of 0.02% buprenorphine formulation from Example 3 was applied directly to the cheek area of the skin just before bed time. The cream after 15 minutes numbed the pain significantly, and the patient slept through the night.

Example 5

Treatment of Resistant Pain with Buprenorphine Formulation

A wheelchair bound patient suffering from years of endometriosis and fibromyalgia had multiple hyperalgesic signs and symptoms including punctate hyperalgesia, allodynia, and tenderness in 10/10 control points and was nonresponsive to morphine, methadone, suboxone and multiple other agents and allergic to adhesive tape. The patient applied 100 mcg BID 0.2% buprenorphine formulation from Example 3 and demonstrated marked improvement, had 3/10 tender control points, and no punctate hyperalgesia or allodynia.

A man with severe fibromyalgia and was allergic to BuTrans adhesive was treated with the formulation from Example 3. The patient showed good improvement after not responding to multiple other agents.

Example 6

Transdermal Anesthetic Formulation in Cannabinoid Base

To the formulation of Example 1, was added bupivacaine hydrochloride at 2%, lidocaine at 5% and epinephrine at 0.05% in the external phase of the formulation of Example 1.

Example 7

Administration of Transdermal Anesthetic Formulation in Cannabinoid Base to Patients with Diabetic Ulcers A small amount of cream prepared in Example 6 was applied to the center of the wound in 40 different patients. The wound and cream are then covered with sheet of transparent Opsite wound dressing. Using a few fingers pressed gently against the surface of the wound dressing, the cream was spread evenly over the wound, covering the wound margin. It is then left for 10 minutes. When the time lapsed, the dressing was removed and the cream was manually wiped away from the site. This results in complete anesthesia at the wound site lasting approximately an hour. The wound was then surgically and sharp debrided at no discomfort to the patient.

Example 8

Transdermal THC and CBD Formulation in Cannabinoid Base

Synthetic THC—To the formulation of Example 1, was added synthetic THC at 1.5% (presolubilized to 2% in polar oil) in the external phase of the formulation of Example 1.

Plant Derived THC and CBD—To the formulation of Example 1, was added plant derived THC and CBD at 1% of each (presolubilized to 3% in polar oil) a ratio of about 1:1 in the external phase of the formulation of Example 1

Example 9

Transdermal THC and CBD Formulation for Treatment of Diabetic Peripheral Neuropathy Synthetic THC Formulation of Example 8 was used by 10 patients who reported a significant decrease in experienced pain. Baseline pain scores were 7-8 out of 10 before application and reduced to 4-5 out of 10 after application. All patients reported a noticeable improvement in the quality and duration of the sleep that they experienced. Results from this study indicated that when sleep quality improved, in addition to the reduction in experienced pain, there was also an improvement in the patient's overall symptomology.

Plant derived THC and CBD Formulation of Example 8 was used by another 10 patients. In addition to reporting a more significant pain reduction that the synthetic THC group, they also reported a significant improvement in the quality and the duration of sleep experienced. None of the patients reported euphoria. However, it is believed that the THC within the cream causes a pseudo euphoric effect that allows them to relax and sleep more soundly.

The subjective results from both sets of patients implied that the plant derived THC-CBD formulation was more successful at reducing pain and improving the quality and duration of sleep in patients suffering from peripheral diabetic neuropathy. All the patients were above the age of 65 years and none reported negative side effects from the use of the cream.

Example 10

Transdermal CBD Formulation in Cannabinoid Base

To the formulation of Example 1, was added hemp oil at 8% in the oil phase of the formulation of Example 1 and 1% CBD in the external phase. Two different sources of CBD were obtained from which two creams, A and B, were formulated.

Example 11

Pharmacokinetics of Transdermal CBD Oil Formulation

Formulations

Formulations—Formulations used: Cream A and B from Example 10 and vehicle were prepared and contained 1% CBD and whereas the vehicle represents the base transdermal formulation.

Animal Manipulations and Dosing

All animal testing was done in accordance with CACC guidelines. Three Sprague-Dawley rats/treatment group (250-325 g) from Charles River Labs were acclimatized for a minimum of 5 days prior to surgery. Body weights were recorded on the day of dosing. Catheters were implanted in the carotid artery (CAC, for serial blood collection) at least one day prior to dosing. The hair from the lower back, covering a target 10% of the total body surface area, was clipped while animals are anesthetized in preparation for transdermal dosing. The test article was applied in a thin, uniform layer to the shaved area of the back, using a spatula. Following application the test article was held in contact with the skin and protected from removal by the animal with a Vet Wrap bandage. 500 mgrams of each cream was applied in this manner using three animals/group.

Blood Collection and Processing

Whole blood collections for pharmacokinetic serum samples was collected from the CAC and the sample volume replaced with saline. Blood samples were collected pre-dose, 0.083, 0.25, 0.5, 1.0, 2.0, 4.0, 6.0, and 8.0 hours post-dosing. All blood samples were transferred into $K_2$EDTA microtainer tubes on wet ice and centrifuged within 5 min (3200×g for 5 min at 4° C.) to obtain plasma. All plasma samples were stored immediately at −80° C. and shipped to Charlottetown, PE on dry ice. Upon receipt samples were immediately transferred to −80 ° C. until processed for analyte quantification.

Chemicals and Reagents

For the quantification of target analytes a series of standards were purchased including cannabidiol (Sigma Aldrich, C-045), tetrahydrocannabinol (Sigma Aldrich, T-005), deuterated cannabidiol-d3 (Sigma Aldrich, C-084), and deuterated tetrahydrocannibindol-d3 (Sigma Aldrich, T-003). Solvents used during sample extraction and processing as well as chromatographic separation included water (Caledon, 8801-7-40), methanol (VWR, CAMX0488-1), acetonitrile (Caledon, 1401-7-40), formic acid (Sigma Aldrich, F0507), glacial acetic acid (BioShop, ACE222), ammonium hydroxide solution (Sigma Aldrich, 221228-100 mL), and Hexane-190 (Caledon, 5502-2-40). For sample processing solid phase extraction of plasma samples Bond-Elute Plexa solid phase columns were utilized (Agilent, 12109603), along with Axygen microcentrifuge tubes (Axygen, MCT-175-C), autosampler vials (Agilent, 51832069), caps (Agilent, 51855863), and microvolume inserts (VWR, 97052-438). For blank and dope tests Sprague-Dawley plasma from BioIVT was used (pooled, male, K2EDTA, non-filtered, RAT00PLK2YNN). Chromatographic separation of analytes was completed using a 100mm×2.1mm and 3.5 µm Zorbax Eclipse-Plus C18 column (Agilent, 959793-902).
Standards The standards cannabidiol (CBD), tetrahydrocannabinol (THC), deuterated cannabidiol-d3 (CBD-d3), and deuterated tetrahydrocannibindol-d3 (THC-d3) were received at room temperature and aliquoted within individual vials and microvolume inserts at 55 µL per vial and stored at −20 ° C. Working stock solutions and standard series samples were prepared fresh each day of analysis and remaining working stock solutions were discarded and not refrozen or otherwise reused.

Internal stock solution, IS-1, (1 µg/mL CBD-d3, 1 µg/mL THC-d3) was prepared by combing 10 uL of CBD-d3 and 10 uL of THC-d3 with 980 uL of Sample Preparation Buffer (0.005% formic acid, 5% water, and 95% methanol). The working Internal Standard Stock (I.S.S.) was constructed by diluting 50 uL of IS-1 in 950 uL of Sample Preparation Buffer (0.005% formic acid, 5% water, and 95% methanol) to yield a 50 ng/mL CBD-d3 and THC-d3 solution. The I.S.S. is used to prepare the Internal Standard Buffer (I.S.B) required for preparation of the standard series as well as doping unknown samples to yield an equimolar concentration in plasma samples and standards. To prepare I.S.B a volume of 500 uL of I.S.S is diluted using 4.5 mL of Sample Preparation Buffer to yield a final solution comprised of 5 ng/mL CBD-d3 and 5 ng/mL CBD-d3.

To prepare the standard series needed for quantification an initial dilution is constructed by adding 10 uL of CBD stock and 10 uL of THC stock to 980 uL of I.S.B to yield a solution comprised of 10 ug/mL CBD and 10 ug/mL THC (along with internal standards courtesy of the I.S.B) A second dilution is prepared by adding 10 uL of this 10 ug/mL mixture to 990 uL of I.S.B to yield solution of 100 ng/mL for both CBD and THC. This 100 ng/mL solution is subsequently diluted 1:1 (100 uL to 100 uL) a total of nine times to yield a standard series composed of 50, 25, 12.5, 6.25, 3.125, 1.56, 0.78, 0.39, and 0.195 ng/mL in autosampler vials with microvolume inserts. As shown in FIG. 1, Chromatograms of (A) Stock solutions containing 1) CBD (6.25 ng/m L: RT—4.1 min, Blue trace), 2) THC (6.25 ng/mL: RT—6.4 min, Blue trace) 3) d3-CBD (5 ng/mL: RT—4.1 min, pink trace) 4) d3-THC (5 ng/mL: RT—6.4 min, Pink trace) (B) blank plasma and (C) blank plasma doped with 1) CBD (5 ng/mL: RT—4.1 min, Blue trace), 2) THC (5 ng/mL: RT—6.4 min, Blue trace) 3) d3-CBD (5 ng/mL: RT—4.1 min, pink trace) 4) d3-THC (5 ng/mL: RT—6.4 min, Pink trace).

Unknown Plasma sample extraction and preparation

All plasma samples were removed from —80 ° C. immediately prior to manipulation. For each sample a volume of 100 uL was placed within an eppendorf tube and 10 uL of I.S.S added, followed by 300 uL of ice cold acetonitrile. The sample was vortex mixed for five seconds and subsequently centrifuged at room temperature at 4,000×g for five minutes. The supernatant was removed and placed within a clean eppendorf tube and 900 uL of 0.2% (v/v) $NH_4OH$ was added to each sample. Prior to solid phase extraction the Bond-Elute tube was washed with 1.0 mL methanol and then equilibrated with 1.0 mL water, allowing each volume to pass via gravity for a period of five minutes. Subsequently the unknown sample was loaded and allowed to gravity flow for five minutes. The SPE column is washed with a 1.0 mL volume of Wash Buffer (1% glacial acetic acid, 20% acetonitrile, and 79% water) by gravity flow for five minutes and subsequently dried using a stream of nitrogen gas. For sample elution a volume of 750 uL of Elution Buffer (1% glacial acetic acid and 99% acetonitrile) was actively pushed using nitrogen gas and this is repeated, yielding a final elution sample of 1.5 mL. Samples were dried to completion using a Centrivap centrifugal evaporator for 2.5 hours at 40° C. All samples are resuspended in 100 uL Sample Preparation Buffer and placed within autosampler vials with microvolume inserts for analysis. Note, there is no dilution factor involved during mathematical quantification.

Doped Plasma Control (5 ng/mL)

To elucidate overall extraction efficiency and matrix effects, a 100 uL volume of control rodent plasma was doped by adding 5 uL of the previously prepared 100 ng/mL CBD and 100 ng/mL THC mixture and adding 9.5 uL of I.S.S. solution. This was performed in triplicate for each set of unknowns processed. These samples were subsequently manipulated equivalently to all tandem unknown samples.

Blank Plasma Control

To elucidate the presence of interfering matrix materials that generate spurious overlapping signals a 100 uL volume of blank (untreated) control rodent plasma is manipulated equivalently and in tandem unknown samples.

True Blank Plasma Control

To elucidate the presence of interfering matrix materials that generate spurious overlapping signals a 100 uL volume of blank (untreated) control rodent plasma is manipulated equivalently to unknown samples except no internal standard solution was added.

Terpene Analysis

To evaluate the general terpene content of the products this class of molecules were detected using GC-MS/FID courtesy of the National Research Council (NRC) of Canada. A mass of 50.4 mgrams of the vehicle formula was placed within a scintillation vial and 5.0 mL water and 5.0 mL hexane-190 was added. The sample was dispersed by vortexing for five minutes and allowed to rest at room temperature for 10 minutes, yielding a clear phase separation. 1.0 mL of the upper organic layer was removed (5 mg/mL) and placed within and autosampler tube. This sample was provided to the NRC and data reported to Delivra in the form of FID and MS chromatograms.

HPLC-MS/MS Conditions

Chromatographic separation was performed on an Agilent Eclipse Plus 95 Å C18 column (4.6×100 mm, 3.5 µm particle size, Agilent 959961-902) with guard column using an isocratic mobile phase of water (0.1% formic acid): acetonitrile (0.1% formic acid) 10:90 at a flow rate of 0.5 mL/min for 11 min. The first 2 minutes was sent to the waste. The column temperature was 40° C., the autosampler temperature was maintained at 4° C. and the injection volume was 20 µL. A 5500 QTRAP from ABSciex equipped with an electrospray ionization (ESI) was used in negative ion mode for detection of CBDA, THCA-A and THCCOOH-d3 and in positive ion mode for CBD, THC, CBD-d3, and THC-d3 with multiple reaction monitoring (MRM) for quantitative analysis. Nitrogen was used as the collision gas and the curtain gas.

In experiment 1 (negative mode), the curtain gas was 30.00 psi, the collision gas was MED, the ion spray voltage was −4500 V, the temperature was 600 ° C., and gas sources 1 and 2 were 50 and 70 psi respectively. The declustering potential was −155 V, the entrance potential was −10.00 V. Quantification was performed using the transitions m/z 357.0→339.0 (CE=−29 V, 100 msec, CXP=−15 V), m/z 357.0→313.0 (CE=−34 V, 100 msec, CXP=−7 V), and m/z 346.2→302.2, (CE=−22 V, 100 msec, CXP=−15 V) for CBDA, THCA-A, and THCCOOH-d3 with retention times 3.9, 8.5, and 3.45 minutes. The 2nd transitions 357.0→179.0 (CE=−30 V, 100 msec, CXP=−15 V), m/z 357.0→245.0 (CE=−43 V, 100 msec, CXP=−5 V) and m/z 346.2→248.1, (CE=−35 V, 100 msec, CXP=−15 V) of each analyte were used to confirm identity of CBDA, THCA-A, and THC-COOH-d3 respectively.

In experiment 2 (positive mode), the curtain gas was 30.00 psi, the collision gas was MED, the ion spray voltage was 4500 V, the temperature was 600° C., and gas sources 1 and 2 were 50 and 70 psi respectively. The de-clustering potential was 100 V, the entrance potential was 10.00 V, and the cell exit potential was 15.00 V. Quantification was performed using the transition m/z 315.0→193.0 (CE=30 V, 100 msec) for both CBD (retention time—4.2 minutes) and THC (retention time—6.8 minutes), and 318.0→196.0 (CE=30 V, 100 msec) for both CBD-d3 (retention time—4.2 minutes) THC-d3 (retention time—6.8 minutes). The 2nd transition 315.0→259.0 (CE=30 V, 100 msec) was used to identification of CBD or THC.

Analytical data was acquired and absolute quantification processing was performed by using Analyst software 1.6.2. and using CBD-d3 and THC-d3 as internal standards for all their respective analytes. For the relative quantification of the unknown cannabinoid species with a retention time of 4.5 minutes the standard series and internal standard signal associated with CBD were used as surrogate quantification parameters.

Results

The existence of ~113 cannabinoid species and the extremely similar structure and molecular weights these species share (e.g. CBD and THC with precursor ions of 313.00 and 313.10, respectively), it is hypothesized that other cannabinoid species may be present and interfering within the quantification of the target analytes. Using the methods described herein the blank plasma samples do not produce interfering signals at the retention time of the analytes or internal standards, although an increase in background was observed in plasma-derived samples, as well as signals at alternative retention times. The method demonstrates linearity from 0.20 ng/mL to 50 ng/mL with a limit of quantification and limit of detection of 0.2 ng/mL for CBD and THC. With respect to doped control samples (5 ng/mL) the relative average inter-assay signal response for CBD and THC is 99.9+/1.6% and 101.9+/−1.8% (mean±/−SEM) (respectively) indicating an acceptable extraction procedure.

Figure 2:
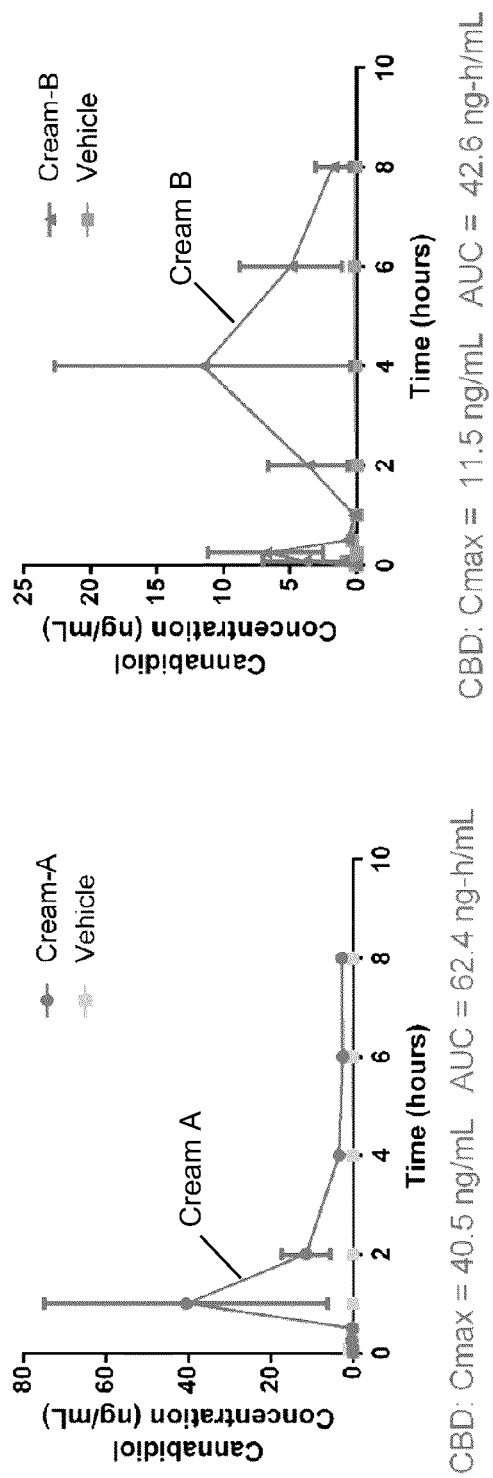
FIG. 2 shows the pharmacokinetics of CBD using a topical cannabis formulation in one embodiment of the disclosure.

Animals treated with Cream-A resulted in a Cmax of 40.5 ng/mL at 1 hour and an overall $AUC_{0-8}$ of 62.4 ng-h/mL (FIG. 2). Cream-B treatment resulted in a Cmax of 11.5 ng/mL at 4 hours and an overall $AUC_{0-8}$ of 42.6 ng-h/mL (FIG. 2). Significant variability between animals is evidenced by the very high standard errors, however the 3.7×higher Cmax in Cream-A may be indicative of a more consistent absorption of active. The most obvious difference between the two groups, however is the tmax (1 h vs 4 h). This may be an artifact of one outlier animal in the Cream-B group. Indeed, in the cream B animals, 2/3 had a Cmax before 1 hours, similar to Cream-A animals. The third animal, however, displayed a higher overall bioavailability, with a relatively high Cmax at 4 hours, resulting in an overall Cmax at the later timepoint and an overall appearance of a two-peaked curve. All animals in both treatment groups had absorption of the active of interest into circulation, with the animal with the lowest Cmax of 5 ng/mL. As shown in FIG. 2, Sprague-Dawley rats were administered Cream-A (0.5 g, n=3) or Cream-B (0.5 g, n=3) and serial blood samples were collected, processed to yield plasma and analyzed for cannabidiol (CBD) concentration using LC/MS/MS. Observed Cmax values were calculated to be 40.5 ng/mL at 1.0 hours for Cream-A and 11.5 ng/mL at 4.0 hours for Cream-B. In addition, three animals were treated with vehicle only as illustrated.

Figure 3:
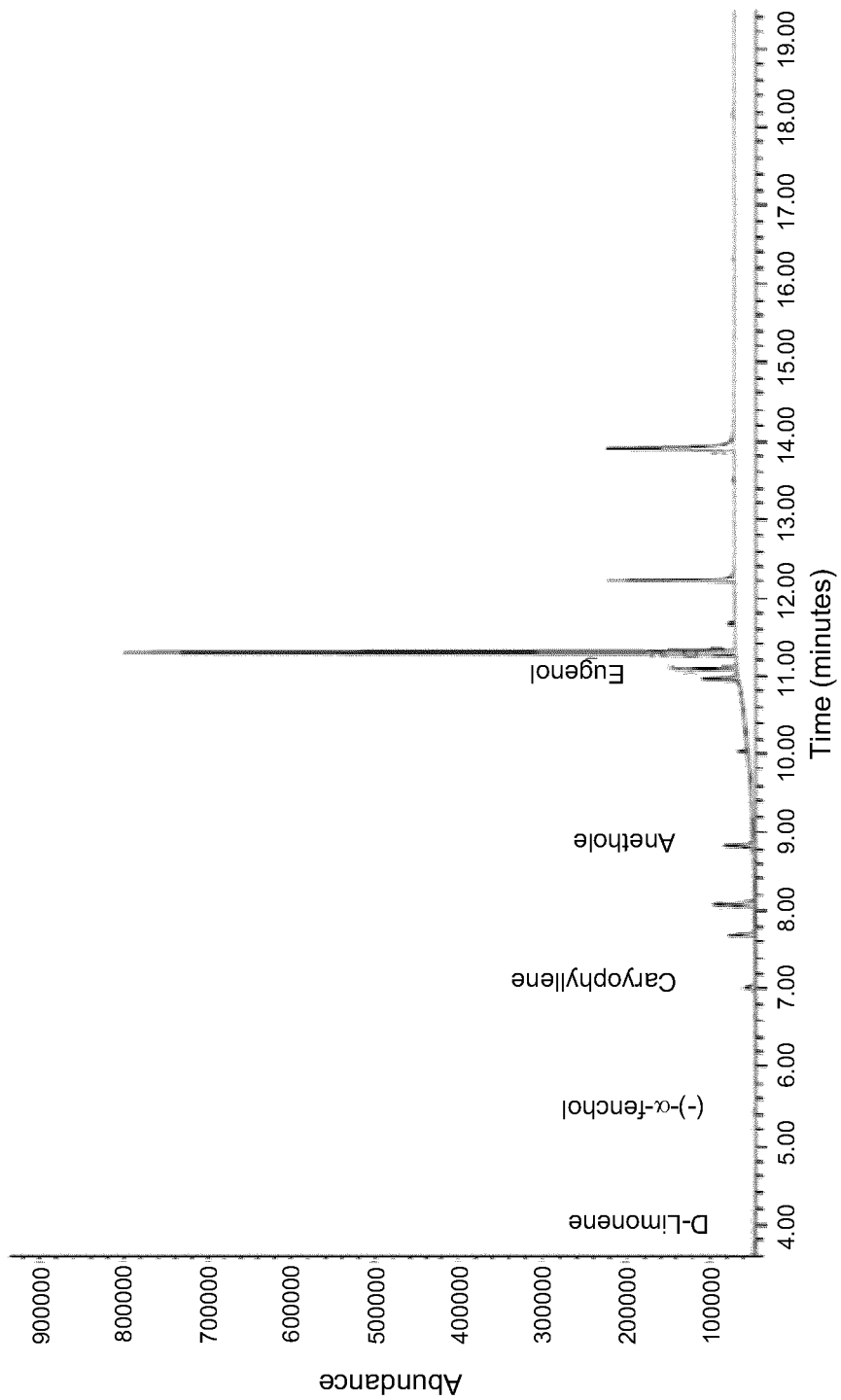
FIG. 3 is a GC-MS/FID general terpene profile.

In addition to the pharmacokinetic assessment of these two formulations, the vehicle formula was evaluated to measure terpene content using GC-MS/FID and identified several terpenes that are reflective of ingredients and typical of *cannabis* extracts (FIG. 3). Specifically, the terpenes identified include eugenol, anethole, caryophyllene, fenchol, and limonene in this this general concentration order (FIG. 3). Of particular note, caryophyllene and limonene are commonly found in *cannabis* extracts.

Discussion

The methods constructed for the quantification of CBD and THC are sufficient to accurately detect and quantify relevant levels of CBD and THC in plasma samples and applicable to pharmacokinetic experimentation. Two different cream formulations, each containing 1% CBD were applied to Sprague-Dawley rats and blood sampled over the following 8 hours displayed very different pharmacokinetic profiles. Although comparable AUC's were observed (62.4 ng-h/mL vs 42.6 ng-h/mL), the Cmax's were very different, 1 vs 4 hours.

Example 12

Cannabinoid Formulation in Oil

Cannabinoids were extracted from the plant using $CO_2$, resulting in an extract comprising THC and CBD in a ratio of 37.22% (w/w) (THC) and 32.21% (w/w) (CBD). The prepared oil formulation contained 6.6% (w/w) of the $CO_2$ cannabinoid extract in a composition comprising a mixture of mono-, di- and triglycerides (40% w/w), argan oil (33.4% w/w) and Transcutol® CG (20% w/w).

Example 13

Pharmacokinetics of Transdermal CBD Oil Formulation

Formulations

The Formulation of Example 12 containing a final concentration of 6.6% (w/w) of a cannabis extract, was used in the following Pharmacokinetic test.

Animal Manipulations and Dosing

Two Sprague-Dawley rats (250-325 g) from Charles River Labs will be acclimatized for a minimum of 5 days prior to surgery. Body weights were recorded on the day of dosing. Catheters were implanted in the carotid artery (CAC, for serial blood collection) at least one day prior to dosing. The hair from the lower back, covering a target 10% of the total body surface area, was clipped while animals are anesthetized in preparation for transdermal dosing. The test article was applied in a thin, uniform layer to the shaved area of the back, using a spatula. Following application the test article was held in contact with the skin and protected from removal by the animal with a Vet Wrap bandage. 0.5 grams of Delivra-8009 was applied in this manner using two animals.

Blood Collection and Processing

Whole blood collections for pharmacokinetic serum samples was collected from the CAC and the sample volume replaced with saline. Blood samples were collected pre-dose, 0.083, 0.25, 0.5, 1.0, 2.0, 4.0, 6.0, and 8.0 hours post-dosing. All blood samples were transferred into $K_2$EDTA microtainer tubes on wet ice and centrifuged within 5 min (3200×g for 5 min at 4° C.) to obtain plasma. All plasma samples were stored immediately at −80° C. and shipped to Charlottetown, PE on dry ice. Upon receipt samples were immediately transferred to -80° C. until processed for analyte quantification.

Chemicals and Reagents

For the quantification of target analytes a series of standards were purchased including cannabidiol (Sigma Aldrich, C-045), tetrahydrocannabinol (Sigma Aldrich, T-005), deuterated cannabidiol-d3 (Sigma Aldrich, C-084), and deuterated tetrahydrocannibindol-d3 (Sigma Aldrich, T-003). Solvents used during sample extraction and processing as well as chromatographic separation included water (Caledon, 8801-7-4C), methanol (VWR, CAMX0488-1), acetonitrile (Caledon, 1401-7-4C), formic acid (Sigma Aldrich, F0507), glacial acetic acid (BioShop, ACE222), and ammonium hydroxide solution (Sigma Aldrich, 320145). For sample processing solid phase extraction of plasma samples Bond-Elute Plexa solid phase columns were utilized (Agilent, 12109603), along with Axygen microcentrifuge tubes (Axygen, MCT-175-C), autosampler vials (Agilent, 51832069), caps (Agilent, 51855863), and microvolume inserts (VWR, 97052-438). Chromatographic separation of analytes was completed using a 100mm×2.1mm and 3.5 μm Xorbax Eclipse-Plus 018 column (Agilent, 959793-902).

Standards

The standards cannabidiol (CBD), tetrahydrocannabinol (THC), deuterated cannabidiol-d3 (CBD-d3), and deuterated tetrahydrocannibindol-d3 (THC-d3) were received at room temperature and aliquoted within individual vials and microvolume inserts at 55 μL per vial and stored at −20° C. Working stock solutions and standard series samples were prepared fresh each day of analysis and remaining working stock solutions were discarded and not refrozen or otherwise reused.

The working Internal Standard Stock (I.S.S.) was constructed by diluting 10 uL of CBD-d3 and 40 uL of THC-d3 with 950 uL of Sample Preparation Buffer (0.005% formic acid, 5% water, and 95% methanol) to yield a 1 ug/mL CBD-d3 and 4 ug/mL THC-d3 solution. Subsequently 50 uL of this solution was diluted using 950 uL of Sample Preparation Buffer to yield the final I.S.S comprised of 50 ng/mL CBD-d3 and 200 ng/mL THC-d3. The I.S.S. is used to prepared the Internal Standard Buffer (I.S.B) required for preparation of the standard series as well as doping unknown samples to yield an equimolar concentration in plasma samples and standards. To prepare I.S.B a volume of 250 uL of I.S.S is diluted using 4.75 mL of Sample Preparation Buffer to yield a final solution comprised of 2.5 ng/mL CBD-d3 and 10 ng/mL CBD-d3.

To prepare the standard series needed for quantification an initial dilution is constructed by adding 10 uL of CBD stock and 10 uL of THC stock to 980 uL of I.S.B to yield a solution comprised of 10 ug/mL CBD and 10 ug/mL THC (along with internal standards courtesy of the I.S.B) A second dilution is prepared by adding 10 uL of this 10 ug/mL mixture to 990 uL of I.S.B to yield solution of 100 ng/mL for both CBD and THC. This 100 ng/mL solution is subsequently diluted 1:1 (100 uL to 100 uL) a total of nine times to yield a standard series composed of 50, 25, 12.5, 6.25, 3.125, 1.56, 0.78, 0.39, and 0.195 ng/mL in autosampler vials with microvolume inserts.

Unknown Plasma Sample Extraction and Preparation

All plasma samples are removed from −80° C. immediately prior to manipulation and remaining volumes (if any) were refrozen at −80° C. For each sample a volume of 100 uL is placed within an eppendorf tube and 5 uL of I.S.S is added, followed by 300 uL of ice cold acetonitrile. The sample is vortex mixed for five seconds and subsequently centrifuged at room temperature at 4,000×g for five minutes. The supernatant is removed and placed within a clean eppendorf tube and 900 uL of 0.2% (v/v) $NH_4OH$ is added to each sample. Prior to solid phase extraction the Bond-Elute tube is equilibrated with 1.0 mL methanol and 1.0 mL water, allowing each volume to pass via gravity for a period of five minutes. Subsequently the unknown sample is loaded and allowed to gravity flow for five minutes. The SPE column is washed with a 1.0 mL volume of Wash Buffer (1% glacial acetic acid, 20% acetonitrile, and 79% water) by gravity flow for five minutes and subsequently dried using a stream of nitrogen gas. For sample elution a volume of 750 uL of Elution Buffer (1% glacial acetic acid and 99% acetonitrile) is actively pushed using nitrogen gas and this is repeated, yielding a final elution sample of 1.5 mL. Samples are dried to completion using a Centrivap centrifugal evaporator for 2.5 hours at 40° C. All samples are resuspended in 100 uL Sample Preparation Buffer and placed within autosampler vials with microvolume inserts for analysis. Note, there is no dilution factor involved during mathematical quantification.

Doped Plasma Control (5 ng/mL)

To elucidate overall extraction efficiency and matrix effects a 100 uL volume of control rodent plasma is doped by adding 5 uL of the previously prepared 100 ng/mL CBD and 100 ng/mL THC mixture. This sample is subsequently manipulated equivalently to all tandem unknown samples, including the addition of 5 uL of I.S.S.

Spiked Plasma Control (5 ng/mL)

To elucidate overall and matrix effects independently of SPE extraction a 100 uL volume of blank (untreated) control rodent plasma is manipulated equivalently and in tandem unknown samples, however the final lyophilized sample is resuspended using 95 uL of Sample Resuspension Buffer along with 5 uL of of the previously prepared 100 ng/mL CBD and 100 ng/mL THC mixture.

Blank Plasma Control

To elucidate the presence of interfering matrix materials that generate spurious overlapping signals a 100 uL volume of blank (untreated) control rodent plasma is manipulated equivalently and in tandem unknown samples.

HPLC-UV Instrumentation and Conditions

Chromatographic separation was performed on an Agilent 1260 chromatography system using ABSciex Analyst software version 1.6.2. Isocratic separation utilized a Xorbax Eclipse-Plus $C_{18}$ column (100mm×2.1mm and 3.5 μm) with guard using a mobile phase of 10% A (0.1% (v/v) formic acid in water) and 90% B (0.005% formic acid, 5% water, and 95% methanol) at a flow rate of 0.5 mL/min for 14 minutes. The first two minutes following injection are sent to the waste with retention times of 4.1 minutes for CBD/CBD-d3 and 10.1 minutes for THC/THC-d3. An unknown hypothetical cannabinoid observed in unknown samples only with a clear pharmacokinetic profile was observed and maintained a retention time of 4.5 minutes. There was no post time. The column temperature was 40° C. and the autosampler temperature was maintained at 4° C. The sample injection volume was 20 μL and the injector is set to −10 mm with bottom sensing enabled.

Mass Spectrometric Instrument and Conditions:

A 5500 QTRAP from AB Sciex Instruments equipped with an electrospray ionization (ESI) was used in the negative ion mode with multiple reaction monitoring (MRM) for the quantitative analysis. Nitrogen was used as the collision gas and the curtain gas. Common settings included curtain gas at 30.00 psi, the collision gas at Medium, ion spray voltage at −4500 volts, temperature set to 600° C., exit potential (EP) set to −10, collision cell exit potential (CXP) set to −15, and gas sources 1 and 2 were 50 and 70 psi, respectively. For quantification analyte specific multiple reaction monitoring (MRM) was employed with unique declustering potentials and collision energies as outlined below:

| Analyte | Precursor Ion (m/z) | Product Ion (m/z) | Dwell time (msec) | Declustering Potential (DP) | Collision Energy (CE) |
|---|---|---|---|---|---|
| CBD | 313.00 | 245.10 | 100.00 | −155.00 | −32.00 |
| CBD-d3 | 316.00 | 248.10 | 100.00 | −155.00 | −32.00 |
| THC | 313.10 | 245.10 | 100.00 | −150.00 | −38.00 |
| THC-d3 | 316.10 | 248.10 | 100.00 | −150.00 | −38.00 |

Quantification Analysis

Analytical data was acquired and absolute quantification processing was performed by using Analyst software 1.6.2. and using CBD-d3 and THC-d3 as internal standards for all their respective analytes. For the relative quantification of the unknown cannabinoid species with a retention time of 4.5 minutes the standard series and internal standard signal associated with CBD were used as surrogate quantification parameters.

Results

Using the methods described herein the blank plasma samples do not produce interfering signals although the background increases from ~50 cps for neat standards to approximately 100 cps for true unknown plasma-derived samples. The method demonstrates linearity from 0.20 ng/mL to 50 ng/mL with a limit of quantification and limit of detection of 0.2 ng/mL for CBD and a limit of detection and limit of quantification of 1.56 ng/mL for THC. With respect to spike control samples (5 ng/mL) the relative average inter-assay signal response for CBD and THC is 98.3% and 142% (respectively) indicating limited matrix interference for the former and possible enhancement for the latter. With respect to dope control samples (5 ng/mL) the relative inter-assay signal response for CBD and THC is 83.9% and 103% (respectively) indicating an acceptable extraction efficiency.

With respect to the quantification of THC, no unknown samples yielded a detectable signal therefore the subsequent results and discussion will focus upon the analysis of CBD and the unknown cannabinoid of similar MRM conditions and retention time.

Figure 4:
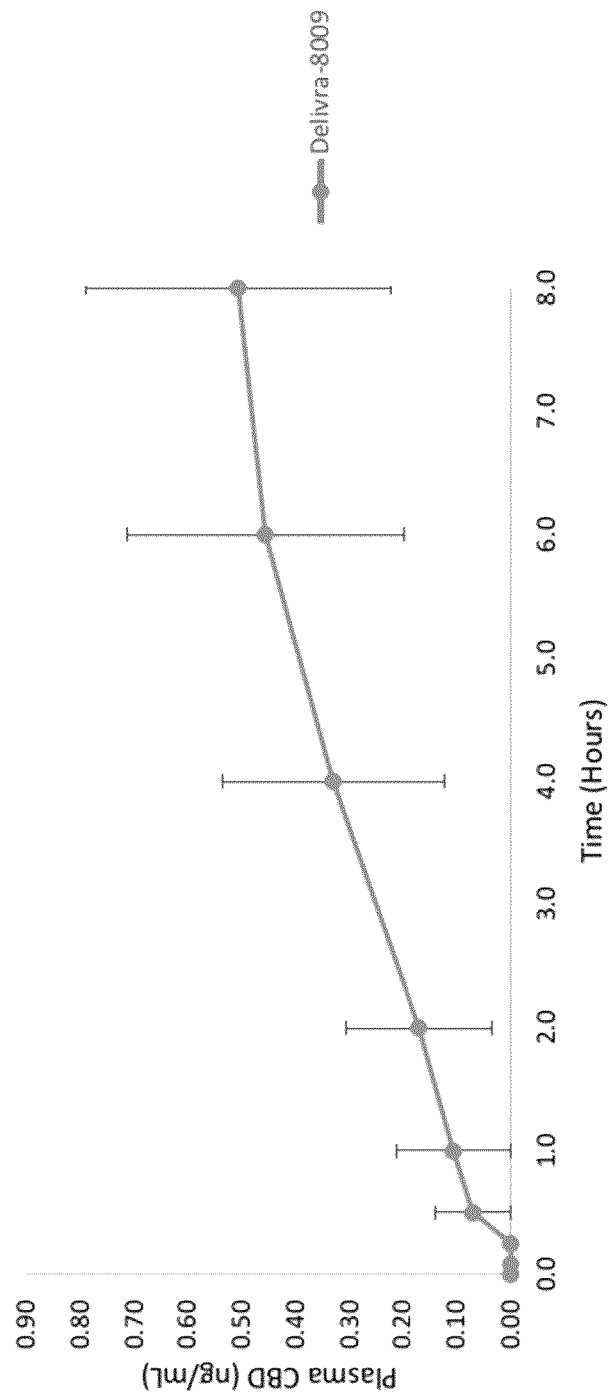
FIG. 4 shows the pharmacokinetics of CBD using a topical cannabis formulation in another embodiment of the disclosure.

The Delivra-8009 formulation produced a clear and consistent peak for all animals with a retention time for CBD of 4.1 minutes and an escalating serum concentration throughout the observed time period (FIG. 4). In addition, a second peak with the same MRM conditions, but unique retention time (4.5 minutes) was identified and quantified based upon CBD standards and demonstrated an initial detection at 0.25 hours, Tmax of 1.0 hours and a Cmax of 0.88 ng/mL (FIG. 5). As shown in FIG. 4, Sprague-Dawley rats were administered Delivra-8009 (0.5 gram, N=2) and serial blood samples were collected, processed to yield plasma and analyzed for Cannabidiol (CBD) concentration using LC/MS/MS. A linearly increasing level of CBD (maximum observed 0.51 ng/mL at 8.0 hours) was quantified for animals treated with Delivra-8009. As shown in FIG. 5, Sprague-Dawley rats were administered Delivra-8009 (0.5 gram, N=2) and serial blood samples were collected, processed to yield plasma and analyzed for relative quantification of an unknown Cannabinoid using LC/MS/MS. The unknown cannabinoid demonstrated a clear kinetic response with initial detection at 0.25 hours, Tmax of 1.0 hours and a Cmax of 0.88 ng/mL.

The methods constructed for the quantification of CBD and THC are sufficient to accurately detect and quantify relevant levels of CBD and THC in plasma samples and applicable to pharmacokinetic experimentation. Although the method can be modified to yield limits of detection and quantification below 0.2 ng/mL it is unclear if such measurements are reflective of biologically relevant value. This is acutely true for THC, in that Delivra-8009 did not yield a detectable level (zero or below 1.5 ng/mL) of this compound and while alterations in the method could heighten detection sensitivity it is unclear if levels below 1.5 ng/mL are relevant to product development.

Delivra-8009 generated a linearly increasing level of CBD in plasma with an initial detection at 0.5 hours post-administration and 0.51 ng/mL at 8.0 hours post-administration. Curiously, a second peak was detected that demonstrated pharmacokinetic characteristics and given the existence of ~113 cannabinoid species and the extremely similar structure and molecular weights these species share (e.g. CBD and THC with precursor ions of 313.00 and 313.10, respectively), it is hypothesized this unknown compound is another cannabinoid. As the MRM pairs for CBD and the unknown are equivalent it is considered highly unlikely that this compound is a metabolite. Analysis of this compound portrayed a dynamic pharmacokinetic profile with initial detection at 0.25 hours, Tmax of 1.0 hours and a Cmax of 0.88 ng/mL. Given the plasma levels of CBD and the unknown cannabinoid compound for Delivra-8009, this formulation can be used as a positive control of dermal tissue analysis should this experimental avenue proceed.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

| Formulation 1 | | |
|---|---|---|
| | Ingredients | % |
| Phase A | Emulsifiers | 5% |
| | Wax Stabilizer | 3% |
| | Polar Emollient Oils | 10% |
| | Anionic emulsifier | 0.6% |
| | Medium Polar Emollient | 3% |
| | Terpene-rich natural butter | 3% |
| Phase B | Water | 58.5% |
| | Humectant | 4% |
| | Thickener | 0.5% |
| Phase C | Preservative | 2% |

TABLE 1-continued

Formulation 1

| | Ingredients | % |
|---|---|---|
| Phase D | Mango extract | 2% |
| | Hops extract | 0.6% |
| | Penetration Enhancer | 1.5% |
| Phase E | Thickener | 1% |
| | Terpene Extracts and Oils | 1.3% |
| Phase F | Phospholipid Complexed Rutin | 2% |
| | Water | 2% |
| | Total | 100.00% |

The invention claimed is:

1. A transdermal emulsion formulation comprising:
(a) an aqueous phase comprising water and at least one emulsion stabilizer selected from natural polymers, gums and synthetic polymers, and mixtures thereof; wherein the natural polymers are selected from alginic acid, cellulose, and scleroglucans, and mixtures thereof, wherein the gums are selected from xanthan gum, tara gum, guar gum and arabic gum, and mixtures thereof, and wherein the synthetic polymers are selected from polyacrylates, polyisobutenes and polysorbates, and mixtures thereof, and wherein the at least one emulsion stabilizer in the aqueous phase is present in an amount of about 0.1 wt % to about 1 wt %;
(b) an oil phase comprising:
at least one emulsifier selected from oil-soluble fatty acid esters or mixtures of fatty acid esters in which the fatty acid esters have a fatty acid composition similar to the fatty acid composition of skin, wherein the oil-soluble fatty acid esters or mixture of fatty acid esters are $C_{14}$-$C_{26}$-fatty acids esterified with a fatty acid alcohol selected from cetyl alcohol, cetaryl alcohol, lauryl alcohol, stearyl alcohol, myristyl alcohol and oleyl alcohol or with a sugar alcohol selected from sorbitol, glycerol, mannitol, inositol, xylitol, erythritol, threitol, arabitol, ribitol, or mixtures thereof, wherein the at least one emulsifier in the oil phase is present in an amount of about 2 wt % to about 8 wt %;
at least one emulsion stabilizer selected from one or more waxes, wherein the at least one emulsion stabilizer in the oil phase is present in an amount of about 1 wt % to about 10 wt %;
at least one emollient comprising at least one flavonoid, wherein the at least one emollient is a natural oil or extract from citrus, *Ginkgo biloba*, tea, wine, cacao, onion, kale, parsley, red beans, broccoli, endive, celery, cranberries, blackberries, red raspberries, blackcurrants, acai, blueberries, bilberries, milk thistle, apples, hawthorn, *Echinacea*, grapes, and/or soy, or wherein the at least one emollient comprising at least one flavonoid in the oil phase is a natural oil or extract from the genera *Rubus, Ribes, Argania, Nymphaea, Peucedanum* or *Imperatoria, Sambucus, Calendula, Butea, Citrus* (e.g. lime), or species or subspecies thereof, and wherein the at least one emollient comprising at least one flavonoid in the oil phase is present in an amount of about 3 wt % to about 15 wt %;
at least one other emollient selected from octyl palmitate, isopropyl stearate, isopropyl palmitate, octyl dodecanol, or mixtures thereof, wherein the at least one other emollient in the oil phase is present in an amount of about 1 wt % to about 10 wt %; and
a terpene-rich natural butter, which is a terpene-rich seed butter, wherein the terpene-rich natural butter in the oil phase is present in an amount of about 1 wt % to about 10 wt %;
wherein the oil and aqueous phase form an emulsion;
(c) an external phase comprising:
at least one terpene-rich extract or oil selected from essential oils or extracts from fruits vegetables, herbs, spices, legumes, leaves, seeds, or mixtures thereof, wherein the at least one terpene-rich extract or oil is present in an amount of about 0.1 wt % to about 10 wt %;
at least one penetration enhancers selected from a glycol, dimethyl isosorbide, or a mixture of glycols and/or dimethylisosorbide, wherein the at least one penetration enhancer is present in an amount of about 1 wt % to about 5 wt %;
a phospholipid-complexed flavonoid, wherein the phospholipid is selected from phosphatidylcholine, phosphatidylethanolamine, phosphatidylinostinol, phosphatidylserine, or mixtures thereof, and wherein the flavonoid is selected from quercetin, myrcetin, apigenin, rutin, or mixtures thereof, wherein the phospholipid-complexed flavonoid is present in an amount of about 1 wt % to about 4 wt %; and
a hydrophobic active agent, wherein the hydrophobic active agent comprises:
nabilone present in an amount of about 0.01 wt % to about 1 wt %;
buprenorphine present in an amount of about 0.001 wt % to about 1 wt %;
bupivacaine present as hydrochloride in an amount of about 0.1 wt % to about 5 wt %;
lidocaine present in an amount of about 0.1 wt % to about 10 wt %;
a combination of bupivacaine, lidocaine and epinephrine, wherein the bupivacaine is present as hydrochloride in an amount of about 0.1 wt % to about 5 wt %, the lidocaine is present in an amount of about 0.1 wt % to about 10 wt %, and the epinephrine is present in an amount of about 0.001 wt % to about 1 wt %;
a synthetic cannabinoid present in an amount of about 0.1 wt % to about 5 wt %.
one or more plant-derived cannabinoids, each present in an amount of about 0.1 wt % to about 5 wt %, optionally wherein the one or more plant-derived cannabinoid is THC, CBD, or a combination of THC and CBD; and
optionally,
(d) at least one preservative phase.

2. The transdermal formulation of claim 1, wherein the formulation comprises at least one preservative.

3. The transdermal formulation of claim 1, wherein the formulations further comprise additional ingredients selected from one or more of pH adjusters or buffering agents, further solvents, solubilizers, chelating agents, pigments, fragrances, humectants and/or solubilizers.

4. The transdermal formulation of claim 1, wherein the terpene-rich natural butter is mango butter.

5. The transdermal formulation of claim 1, wherein the terpene-rich extract or oil is an essential oil or an extract from mango, hops, clove, myrtle lemon, black pepper, fennel, and mixtures thereof.

6. A method for the transdermal administration of one or more hydrophobic active agents comprising administering an effecting amount of a formulation of claim 1 to a subject in need thereof.

7. A method for the buccal or rectal administration of one or more hydrophobic active agents comprising administering an effecting amount of a formulation of claim 1 to a subject in need thereof.

8. The transdermal formulation of claim 1, wherein the at least one emulsion stabilizer in the aqueous phase is present in an amount of about 0.2 wt % to about 0.8 wt %.

9. The transdermal formulation of claim 1, wherein the at least one emulsifier in the oil phase is present in an amount of about 4 wt % to about 6 wt %.

10. The transdermal formulation of claim 1, wherein the at least one emulsion stabilizer in the oil phase is present in an amount of about 2 wt % to about 8 wt %.

11. The transdermal formulation of claim 1, wherein:
the at least one emollient comprising at least one flavonoid in the oil phase is present in an amount of about 5 wt % to about 12 wt %; or
the at least one other emollient in the oil phase is present in an amount of about 3 w% to about 5 w%.

12. The transdermal formulation of claim 1, wherein terpene-rich natural butter in the oil phase is present in an amount of about 2 w% to about 5 w%, or about 3 w%.

13. The transdermal formulation of claim 1, wherein the penetration enhancer is ethoxydiglycol.

14. The transdermal formulation of claim 1, wherein:
the at least one terpene-rich extract or oil is present in an amount of about 0.2 wt % to 5 wt %; or
the penetration enhancer is present in an amount of about 1 wt % to about 2 wt %; or
the phospholipid-complexed flavonoid is present in an amount of about 1.5 w% to about 2.5 w%.

15. The transdermal formulation of claim 1, wherein:
the hydrophobic active agent is nabilone present in an amount of about 0.05 wt % to about 0.5 wt %, or about 0.05 wt %;
the hydrophobic active agent is buprenorphine present in an amount of about 0.01 wt % to about 0.05 wt %, or about 0.02 wt %;
the hydrophobic active agent is bupivacaine present as hydrochloride in an amount of about 1.0 w t% to about 3.0 wt %, or about 2.0 wt %;
the hydrophobic active agent is lidocaine present in an amount of about 2.0 wt % to about 8.0 wt %, or about 5.0 wt %;
a combination of bupivacaine, lidocaine and epinephrine, wherein the bupivacaine is present as hydrochloride in an amount of about 1.0 wt % to about 3.0 wt %, or about 2.0 wt %, the lidocaine is present in an amount of a about 2.0 wt % to about 8.0 wt %, or about 5.0 wt %, and the epinephrine is present in an amount of about 0.01 wt % to about 0.05 wt %, or about 0.05 wt %; or
the hydrophobic active agent is the synthetic cannabinoid present in an amount of about 1.0 wt % to about 3.0 wt %, or about 1.5 wt %.

16. The transdermal formulation of claim 1, wherein:
the transdermal formulation further comprises an oily vehicle comprising mono-, di- and triglycerides,
optionally wherein the oily vehicle is obtained by alcoholysis between glycerol and refined corn oil, followed by winterization to remove saturated mono-, di- and triglycerides;
optionally wherein the oily vehicle comprises:
i) about 25-75% (or about 32-52%) of monoglycerides of oleic and linoleic acid;
ii) about 25-75% (or about 40-55%) of diglycerides of oleic and linoleic acid; and
iii) about 1-50% (or about 5-20%) of triglycerides of oleic and linoleic acid; or the hydrophobic active agent is pre-solubilized in an oil formulation, the oil formulation comprising:
i) the hydrophobic active agent;
ii) an oily vehicle comprising mono-, di- and triglycerides;
iii) at least one polar oil, optionally argan oil, sunflower oil, olive oil, avocado oil or jojoba oil; and
iv) the penetration enhancer; or
the hydrophobic active agent is pre-solubilized in an oil formulation, the oil formulation comprising:
i) the hydrophobic active agent comprises a cannabinoid or terpene, wherein the cannabinoid is $CO_2$ extracted, in an amount between about 5-10% (w/w), or about 6.6%;
ii) an oily vehicle comprising mono-, di- and triglycerides in an amount between about 20%-60%, or about 40.0%;
iii) a polar oil, optionally argan oil, sunflower oil, olive oil, avocado oil or jojoba oil, present in an amount between about 25%-50%, or about 33.4%; and
iv) the penetration enhancer, present in an amount between about 10%-30%, or about 20.0%.

17. The transdermal formulation of claim 16, wherein the penetration enhancer is 2-(2-Ethoxyethoxy)ethanol.

18. The transdermal formulation of claim 1, wherein:
the at least one emulsion stabilizer in the aqueous phase comprises xanthan gum;
the at least one emulsion stabilizer in the oil phase comprises one or more plant waxes derived from olives or from palm;
the at least one other emollient in the oil phase comprises isopropyl palmitate;
the terpene-rich natural butter in the oil phase is mango butter; the at least one terpene-rich extract or oil is an essential oil or an extract from mango, hops, clove, myrtle lemon, black pepper, fennel, or a combination of two or more thereof; and
the at least one penetration enhancer comprises ethoxydiglycol.

19. The transdermal emulsion formulation of claim 1, wherein:
the at least one emulsion stabilizer in the aqueous phase is present in an amount of about 0.2 wt % to about 0.8 wt %;
the at least one emulsifier in the oil phase is present in an amount of about 4 wt % to about 6 wt %;
the at least one emulsion stabilizer in the oil phase is present in an amount of about 2 wt % to about 8 wt %;
the at least one emollient comprising at least one flavonoid in the oil phase is present in an amount of about 5 wt % to about 12 wt %;
the at least one other emollient in the oil phase is present in an amount of about 3 wt % to about 5 wt %;
the terpene-rich natural butter in the oil phase is present in an amount of about 2 wt % to about 5 wt %;the at least one terpene-rich extract or oil is present in an amount of about 0.2 wt % to about 5 wt %;
the at least one penetration enhancer is present in an amount of about 1 wt % to about 2 wt %; and
the phospholipid-complexed flavonoid is present in an amount of about 1.5 wt % to about 2.5 wt %.

20. The transdermal emulsion formulation of claim 1, wherein the hydrophobic active agent is THC, CBD, or a combination of THC and CBD present at a ratio of between about 0.1:5.0 to 5.0:0.1, or about 1:1.

* * * * *